US011830607B2

(12) United States Patent
Smith et al.

(10) Patent No.: US 11,830,607 B2
(45) Date of Patent: Nov. 28, 2023

(54) SYSTEMS AND METHODS FOR FACILITATING IMAGE FINDING ANALYSIS

(71) Applicant: AI METRICS, LLC, Hoover, AL (US)

(72) Inventors: Andrew Dennis Smith, Hoover, AL (US); Robert B. Jacobus, Mountain Brook, AL (US); Paige Elaine Severino, Birmingham, AL (US)

(73) Assignee: AI METRICS, LLC, Hoover, AL (US)

( * ) Notice: Subject to any disclaimer, the term of this patent is extended or adjusted under 35 U.S.C. 154(b) by 0 days.

(21) Appl. No.: 17/939,619

(22) Filed: Sep. 7, 2022

(65) Prior Publication Data

US 2023/0076821 A1     Mar. 9, 2023

Related U.S. Application Data

(60) Provisional application No. 63/241,858, filed on Sep. 8, 2021.

(51) Int. Cl.

| | |
|---|---|
| *G16H 30/40* | (2018.01) |
| *G10L 15/26* | (2006.01) |
| *G06T 7/11* | (2017.01) |
| *G06T 7/00* | (2017.01) |
| *G16H 15/00* | (2018.01) |
| *G16H 30/20* | (2018.01) |
| *G16H 50/20* | (2018.01) |

(52) U.S. Cl.
CPC .......... *G16H 30/40* (2018.01); *G06T 7/0012* (2013.01); *G06T 7/11* (2017.01); *G10L 15/26* (2013.01); *G16H 15/00* (2018.01); *G16H 30/20* (2018.01); *G16H 50/20* (2018.01); *G06T 2207/30096* (2013.01)

(58) Field of Classification Search
CPC ........ G16H 30/40; G16H 15/00; G16H 30/20; G16H 50/20; G06T 7/0012; G06T 7/11; G06T 2207/30096; G10L 15/26
See application file for complete search history.

(56) References Cited

U.S. PATENT DOCUMENTS

| | | | |
|---|---|---|---|
| 6,226,422 B1 | 5/2001 | Oliver | |
| 6,514,201 B1* | 2/2003 | Greenberg | .......... G01S 7/52023 600/437 |

(Continued)

OTHER PUBLICATIONS

International Search Report and Written Opinion received for PCT Patent Application No. PCT/US22/76124, dated Nov. 25, 2022, 11 pages.

(Continued)

*Primary Examiner* — Nay A Maung
*Assistant Examiner* — Jose M Torres
(74) *Attorney, Agent, or Firm* — Workman Nydegger

(57) ABSTRACT

A system for facilitating image finding analysis includes one or more processors and one or more hardware storage devices storing instructions that are executable by the one or more processors to configure the system to perform acts such as (i) presenting an image on a user interface, the image being one of a plurality of images provided on the user interface in a navigable format, (ii) obtaining a voice annotation for the image, the voice annotation being based on a voice signal of a user, and (iii) binding the voice annotation to at least one aspect of the image, wherein the binding modifies metadata of the image based on the voice annotation.

20 Claims, 22 Drawing Sheets

(56) References Cited

U.S. PATENT DOCUMENTS

| | | | |
|---|---|---|---|
| 2004/0032531 A1 | 2/2004 | Mercier | |
| 2007/0033535 A1* | 2/2007 | Cornacchia, III | G16H 15/00 |
| | | | 715/780 |
| 2007/0258642 A1 | 11/2007 | Thota | |
| 2010/0266174 A1 | 10/2010 | Lobregt et al. | |
| 2014/0257854 A1 | 9/2014 | Becker et al. | |
| 2016/0350919 A1 | 12/2016 | Steigauf et al. | |
| 2017/0132497 A1 | 5/2017 | Santos et al. | |
| 2017/0200270 A1* | 7/2017 | Reicher | G16H 30/20 |
| 2020/0160982 A1* | 5/2020 | Gurson | G06N 3/08 |
| 2020/0175961 A1* | 6/2020 | Thomson | G10L 15/28 |
| 2021/0166805 A1* | 6/2021 | Knoplioch | G06T 7/0012 |
| 2021/0216822 A1* | 7/2021 | Paik | G06T 7/0012 |

OTHER PUBLICATIONS

Wong. K.L. et al., "Deep learning-based cardiovascular image diagnosis: A promising challenge," Future Generation Computer Systems, vol. 110, Sep. 2020, pp. 802-811.

* cited by examiner

Oncologic Provider Report

Patient: Colorectal Difficult Demo | MRN#: 1052 | 4/23/60 | y | F
Image Exam(s): CAP AX on 2018-04-17
Baseline

Response: None
Criteria: Metastatic Disease

*[bar chart: 2.7 cm baseline/lowest on 4/17/18, Study Date]*

Tumor Burden

| | |
|---|---|
| Current Sum | 2.7 cm |
| % Change from Baseline | N/A |
| % Change from Lowest | N/A |
| % Change from Prior | N/A |

Notes
None
Report not signed off

1602

New Sites of Disease      No

Target Lesions

Liver Right Lobe
☐ Obstructs right biliary    2.7 × 2.2 cm
   ducts

Non-Target Lesions
No Non-Target Lesions

Other Findings

Biliary Intrahepatic
(Moderate right biliary dilatation)
Newly Identified

Large Ascites (Not loculated)
Newly Identified

1604

Reader:
Status: Draft

SYSTEMS AND METHODS FOR FACILITATING IMAGE FINDING ANALYSIS

CROSS-REFERENCE TO RELATED APPLICATIONS

This application claims priority to U.S. Provisional Application No. 63/241,858 filed on Sep. 8, 2021 and entitled "SYSTEMS AND METHODS FOR FACILITATING IMAGE FINDING ANALYSIS", which is incorporated herein by reference in its entirety.

BACKGROUND

Assessment of changes in tumor burden is an important feature for defining tumor response in clinical practice and clinical trials. Both tumor shrinkage and development of disease progression are important endpoints in clinical practice and clinical trials as these often determine objective response to treatment. In order to standardize tumor response assessment, various response criteria have been described, including Response Evaluation Criteria in Solid Tumors (RECIST) version 1.0 or more commonly version 1.1, modified RECIST (mRECIST), World Health Organization (WHO) Criteria, Choi Criteria, Vascular Tumor Burden (VTB) Criteria, Morphology Attenuation Size and Structure (MASS) Criteria, immune-related Response Criteria (irRC), immune RECIST (iRECIST), immune-related RECIST (irRECIST), Cheson Criteria, Lugano Classification lymphoma response criteria, International Working Group consensus response evaluation criteria in lymphoma (RECIL), Positron Emission Tomography Response Criteria in Solid Tumors (PERCIST), European Organization for Research and Treatment of Cancer (EORTC) Response Criteria, Prostate Cancer Working Group 3 (PCWG3) criteria, Response Assessment in Neuro-Oncology (RANO) Criteria, immune RANO (iRANO), International Myeloma Working Group (IMWG) consensus criteria, etc.

In order to assess objective response, an estimate of the overall tumor burden at baseline is needed and used as a comparator for subsequent measurements. Each tumor response criteria specifies parameters that define a measurable lesion at baseline. For example, RECIST 1.1 defines a non-nodal lesion as measurable if it measures cm in long axis at baseline and defines a lymph node as measurable if it measures 0.5 cm in short axis at baseline. When one or more measurable lesions are present at baseline, each tumor response criteria specifies which lesions should be considered as target lesions. Target lesions are typically selected based on being the largest in size or most metabolically active but also should lend themselves to reproducible repeated measurements. Most tumor response criteria limit the number of total target lesions and limit the number of target lesions per organ. For example, RECIST 1.1 limits the total number of target lesions to 5 and the total number of target lesions per organ to 2. Each tumor response criteria specifies how the target lesions should be measured. For example, RECIST 1.1 states that non-nodal lesions should be measured in the longest dimension on axial cross-sectional images, while lymph nodes should be measured in short axis on axial cross-sectional images. The total tumor burden is then a mathematical calculation made from the individual target lesions. For example, the sum of the diameters (longest for non-nodal lesions, short axis for nodal lesions) for all target lesions is calculated and reported as the baseline sum diameters per RECIST 1.1.

The baseline measurements are used as a reference to characterize objective tumor regression or progression in the measurable dimension of the disease. All other lesions (or sites of disease) are identified as non-target lesions. The site of disease of all non-target lesions should be recorded at baseline. At subsequent time points, measurement of non-target lesions is not required, and these lesions are typically followed and defined as 'complete response' (CR), 'unequivocal progressive disease' (PD), 'non-CR/non-PD', or 'not evaluable' (NE). Alternatively, the non-target lesions could be qualitatively evaluated, such as 'present', 'absent', 'larger', or 'smaller'.

While most tumor response criteria utilize measured changes in target lesion length or size as a means of defining objective response, some criteria (e.g., Lugano, PERCIST and EORTC Response Criteria) utilize measured changes in target lesions radiotracer activity as a means of defining objective response, and other criteria use a combination of both. Different tumor response criteria may utilize different metrics, mathematical calculations, or cut points to define objective response, and computer implemented methods that automate one or more processes or method acts and/or ensure user compliance with one or more criteria may be used to reduce errors and improve efficiency in tumor response assessment.

A critical component of any tumor response criteria is the choice of target lesions on the baseline exam. In clinical practice and clinical trials, the choice of target lesions is at the discretion of the physician reviewer, which could be a radiologist, oncologist, radiation oncologist, surgeon, etc. Most tumor response criteria provide guidance on target lesion selection. For example, RECIST 1.1 provides guidance on which lesions are measurable or non-measurable and then provides additional details on how to select target lesions. In general target lesions and lymph nodes are selected based on their size, though the target lesions must be representative of all involved organs and should lend themselves to reproducible repeated measurements. Furthermore, tracking of target lesions over time is advantageous for obtaining accurate and precise objective response.

Conventional methods for tracking lesions (e.g., target lesions and/or non-target lesions) include navigating to an appropriate cross-sectional image, identifying a lesion for analysis, and recording the size of the lesion, the organ location in which the lesion resides, and the image number or slice position of the cross-sectional image depicting the identified lesion.

To track lesions over time, a reviewing physician typically navigates through cross-sectional images captured at a later timepoint to find an image that depicts the same lesion analyzed previously. The reviewing physician then repeats the processes of determining the size of the lesion and recording the organ location, often also recording image number or slice position with or without the series number or name. Often, an additional step of preparing a report for oncological or patient review must be performed by the reviewing physician or another entity.

In some instances, while analyzing lesions according to a predefined tumor response criterion, medical practitioners come across other findings that are relevant to the health status of the patient (even where such findings are not usable as target or non-target lesions of a tumor response criterion). For example, a medical practitioner may discover ascites while assessing a set of CT images for a patient. It is often advantageous to track the progression of such other findings over time, similar to the manner in which target lesions and/or non-target lesions are tracked over time according to tumor response criteria.

However, conventional techniques for analyzing such other findings suffer from a number of shortcomings. For example, existing approaches include manually typing or dictating notes describing other findings into text documents in parallel with image analysis software. Such approaches are often inefficient, requiring the medical practitioner to rapidly switch between different software applications, and often give rise to text and/or dictation errors that can be difficult for the medical practitioner to detect. Furthermore, different medical practitioners often record notes related to other findings in different manners (e.g., using long-form paragraphs or bulleted lists, using different schema for ordering the findings, etc.), which can cause inconsistencies, inefficiencies, and/or inaccuracies when a different medical practitioner analyzes the other findings in subsequent-timepoint images.

Existing techniques for analyzing the other findings in subsequent-timepoint images include providing the text document(s) to a subsequent reviewer to parse the notes, identify portions of the notes relevant to the other findings, search through the subsequent-timepoint images for relevant images that are likely to have captured the other findings (if such other findings remain present at the subsequent timepoint), and analyze the relevant images to determine presence and/or status of the other findings. As noted above, such techniques are prone to error and inefficiency.

Therefore, there exists a substantial need for improved techniques for facilitating image finding analysis and reporting, particularly for baseline and/or longitudinal assessment of image findings that do not fit squarely within a tumor response criterion.

The subject matter claimed herein is not limited to embodiments that solve any disadvantages or that operate only in environments such as those described above. Rather, this background is only provided to illustrate one exemplary technology area where some embodiments described herein may be practiced.

BRIEF DESCRIPTION OF THE DRAWINGS

To further clarify the above and other features of the embodiments described herein, a more particular description will be rendered by reference to the appended drawings. It is appreciated that these drawings depict only examples of the embodiments described herein and are therefore not to be considered limiting of its scope. The embodiments will be described and explained with additional specificity and detail through the use of the accompanying drawings in which:

FIG. 16 illustrates an example report that includes voice annotations for analyzed lesions;

FIG. 18 illustrates an example of analyzing the other finding of FIGS. 10-12 in a corresponding subsequent-timepoint cross-sectional medical image;

DETAILED DESCRIPTION

Figure 1:
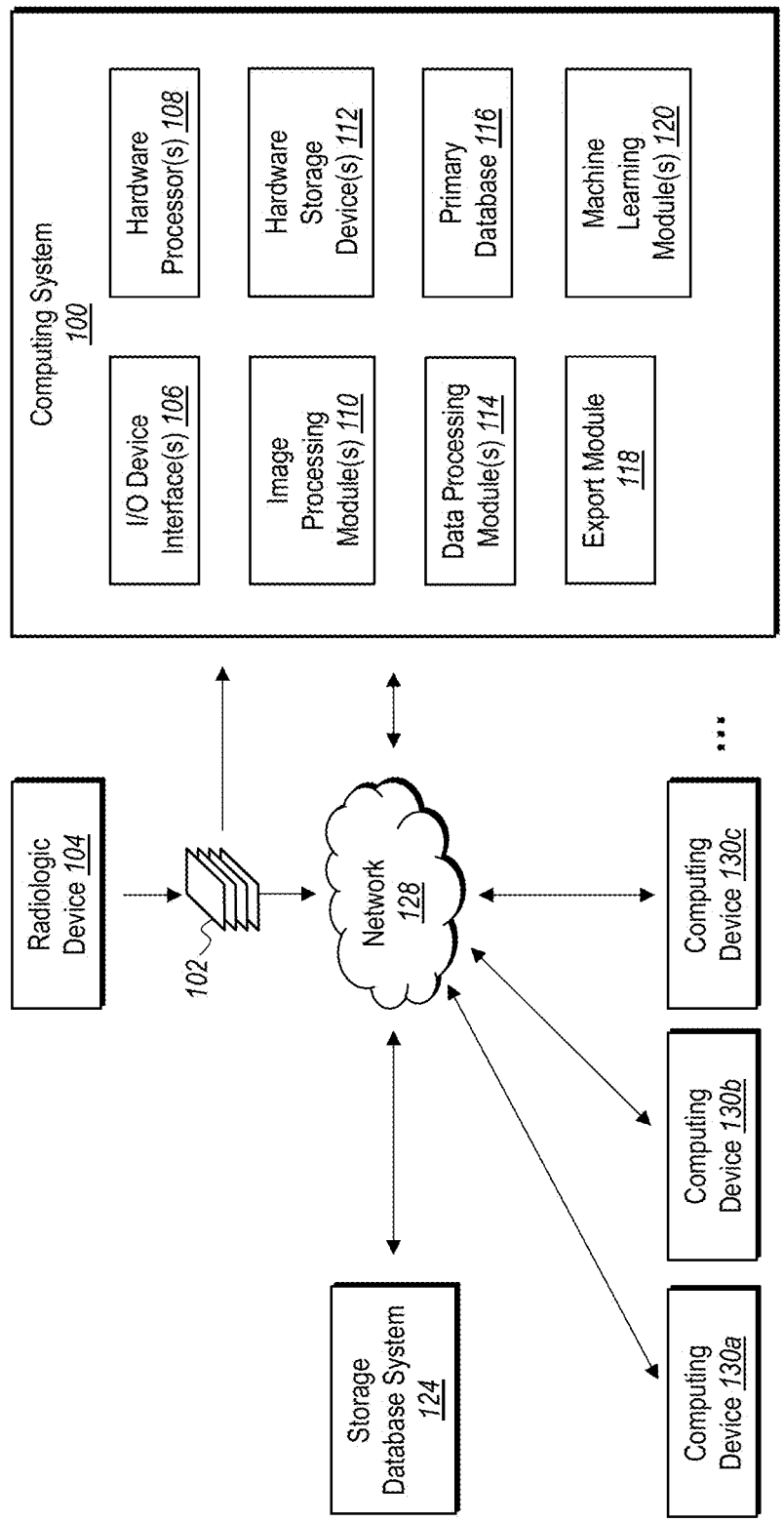
FIG. 1 illustrates a schematic representation of a system for facilitating lesion analysis using one or more cross-sectional images.

While the detailed description may be separated into sections, the contents within each section are not intended to be self-contained descriptions and embodiments. Rather, the contents of each section within the detailed description are intended to be read and understood as a collective whole where elements of one section may pertain to and/or inform other sections. Accordingly, embodiments specifically disclosed within one section may also relate to and/or serve as additional and/or alternative embodiments in another section having the same and/or similar systems, modules, devices, methods, and/or terminology.

The embodiments disclosed herein will now be described by reference to some more detailed embodiments, with occasional reference to any applicable accompanying drawings. These embodiments may, however, be embodied in different forms and should not be construed as limited to the embodiments set forth herein. Rather, these embodiments are provided so that this disclosure will be thorough and complete, and will fully convey the scope of the embodiments to those skilled in the art.

Examples of Technical Benefits, Improvements, and Practical Applications

Those skilled in the art will recognize, in view of the present disclosure, that at least some of the disclosed embodiments may be implemented to address various shortcomings associated with facilitating lesion analysis. The following section outlines some example improvements and/or practical applications provided by the disclosed embodiments. It will be appreciated, however, that the following are examples only and that the embodiments described herein are in no way limited to the example improvements discussed herein.

At least some embodiments disclosed herein include or are configured to perform various acts, such as presenting an image at a user interface, obtaining a voice annotation for the image (based on a voice signal of a user) and binding the voice annotation to at least one aspect of the image. Binding the voice annotation to the at least one aspect of the image modifies metadata of the image based on the voice annotation. In some instances, the image may comprise a cross-sectional medical image that captures one or more structures (e.g., one or more lesions, masses, lymph nodes, metastases, etc.). The voice annotation may take on various forms, such as a transcription of a user dictation, or a voice-driven selection of one or more predefined attributes for structures captured in images (e.g., anatomical location, structure type). A representation of the voice annotation may be presented to the user contemporaneous with at least a portion of the image, which may advantageously allow the user to readily detect dictation errors where they occur.

By building voice annotations into the metadata of the image file, the voice annotations may be readily accessed to facilitate longitudinal analysis of findings within the image file described by or otherwise associated with the voice annotations. For example, at least some embodiments disclosed herein include or are configured to perform acts of presenting a first image of a first plurality of images associated with a first timepoint and presenting a second image of a second plurality of images associated with a second timepoint (subsequent to the first timepoint). The first image includes a structure, and the second image may be presented at least partially for the purpose of evaluating presence and/or status of the structure within the second image. The acts may further include obtaining first metadata for the first image, which describes one or more aspects of the structure and includes a first voice annotation (based on a first human voice signal obtained during first analysis of the first image). The acts may further include presenting a representation of the first voice annotation contemporaneous with the structure (of the first image) and the second image to allow a user to evaluate the presence and/or status of the structure in the second image.

Therefore, implementations of the present disclosure may, in at least some circumstances, facilitate rapid, accurate analysis of structures found within sets of images, even across image sets associated with different timepoints.

The methods and systems of the present disclosure may be useful for evaluating tumor response to chemotherapy, targeted therapy, immunotherapy, radiation therapy, surgical therapy, ablative therapy, hyperthermia therapy, photodynamic therapy, laser therapy, gene therapy, biologic vector therapy, artificial vector therapy, and other forms of therapy. Further, the methods and systems of the present disclosure are applicable and useful to evaluate primary tumors, locoregional spread of tumors, and metastatic tumors; benign and malignant tumors; and a variety of tumor types, including: skin cancer, lung cancer, prostate cancer, breast cancer, colorectal cancer, kidney cancer, lymphoma, thyroid cancer, brain cancer, bone cancer, connective tissue cancer, muscle cancer, liver cancer, gastrointestinal cancer, pancreatic cancer, esophageal cancer, stomach cancer, melanoma, gynecologic cancer, cardiac cancer, and/or others.

Although the present disclosure focuses, in at least some respects, on analysis of lesions within cross-sectional medical images, one will appreciate, in view of the present disclosure, that the principles disclosed herein are not limited thereto and may be applied in other imaging contexts where objects represented in images are annotated and/or notes/transcriptions are obtained therefor.

Having just described some of the various high-level features and benefits of the disclosed embodiments, attention will now be directed to FIGS. 1 through 22. These Figures illustrate various conceptual representations, architectures, methods, and supporting illustrations related to the disclosed embodiments.

Systems for Facilitating Image Finding Analysis

Referring now to FIG. 1, depicted is a schematic representation of a system for facilitating lesion analysis using one or more cross-sectional images, which can implement or serve as a basis for one or more embodiments of the present disclosure. FIG. 1, generally, includes a computing system 100 configured for use in facilitating lesion analysis. In a basic configuration, a computing system includes one or more hardware processors and one or more hardware storage devices that have computer-executable instructions stored thereon. The one or more processors may execute the computer-executable instructions to cause the computing system to perform certain functions and/or operations. A computing system may be in wired or wireless communication (e.g., via a network) with one or more other devices, such as other computing systems or processing centers, storage devices or databases, sensors or sensor systems (e.g., cameras and/or imaging devices), etc. to facilitate carrying out the operations detailed in the computer-executable instructions. Additional details concerning components of computing systems and computing environments will be described hereinafter.

Referring again to FIG. 1, a computing system 100 for carrying out lesion analysis is depicted as including various components, including hardware processor(s) 108, hardware storage device(s) 112, I/O device interface(s) 106, image processing module(s) 110, data processing module(s) 114, export module 118, primary database 116, and/or machine learning module(s) 120. It will be appreciated, however, that a system 100 for facilitating lesion analysis may comprise any number of additional or alternative components.

As used herein, the terms "executable module," "executable component," "component," "module," or "engine" can refer to any combination of hardware components or software objects, routines, or methods that may configure a computer system 100 to carry out certain acts. For instance, the different components, modules, engines, devices, and services described herein may be implemented as objects or processors that execute on computer system 100 (e.g. as separate threads). While FIG. 1 depicts several independent modules 110, 114, 118, 120, one will understand the characterization of a module is at least somewhat arbitrary. In at least one implementation, the various modules 110, 114, 118, 120 of FIG. 1 may be combined, divided, or excluded in configurations other than that which is shown. For example, any of the functions described herein with reference to any particular module 110, 114, 118, 120 may be performed by any number and/or combination of processing units, software objects, modules, computing centers (e.g., computing centers that are remote to computing system 100), etcetera. As used herein, the individual modules 110, 114, 118, 120 are provided for the sake of clarity and explanation and are not intended to be limiting.

The computing system 100 may obtain one or more cross-sectional medical images 102 for analysis of lesions represented in the cross-sectional images 102. The cross-sectional medical images may be captured by a radiologic device 104. In some implementations, the radiologic device 104 and the computing system 100 are physically connected such that the one or more cross-sectional images 102 are transferred directly via the physical connection. Alternatively, or additionally, the computing system 100 can obtain the cross-sectional images 102 indirectly via a network 128 to which both the radiologic device 104 and the computing system 100 are connected (whether via wired connections, wireless connections, or some combination), as known in the art. The network 128 may be any number of private networks, such as an intranet of a hospital or a private cloud or server, or the network 128 may be any number of public networks, such as a public cloud or any other public network accessible via an internet connection.

The radiologic device 104 illustrated in FIG. 1 can include any medical imaging device that generates cross-sectional images. By way of non-limiting example, a radiologic device 104 may comprise at least one of: x-ray computed tomography (CT), computed tomography perfusion (CTP) imaging, positron emission tomography (PET), single-photon emission computed tomography (SPECT), magnetic resonance imaging (MRI), or ultrasound. Consequently, in some instances, the cross-sectional images may include digital medical image data in the form of: CT images, CTP images, PET images, SPECT images, MRI images, or ultrasound images, respectively. Other formats (whether cross-sectional or not) are contemplated by the present disclosure, such as radiographs, nuclear scintigraphy, angiography, fluoroscopy, echocardiograms, endoscopic images, and/or others. One will appreciate, in view of the present disclosure, that the principles disclosed herein can be implemented in association with any type of image modality captured using any suitable imaging device(s).

Upon obtaining the cross-sectional images 102, the computing system 100 may store the cross-sectional images 102 in a primary database 116 or a hardware storage device 112 for immediate or later access and/or lesion analysis. In some instances, at least some of the cross-sectional images 102 are not stored on storage media that are local to the computing system 100 (e.g., primary database 116, hardware storage device(s) 112), but rather remain stored on remote computer-readable media such as storage database system 124, hardware storage device(s) of a remote computing device 130a, 130b, 130c, and/or any other remote repository. Those skilled in the art will recognize that in such and/or other instances, the operations associated with lesions analysis described herein referring to computing system 100 may be performed in a distributed and/or asynchronous manner by various computing devices.

As will be described in more detail with reference to FIGS. 2-19, the computing system 100 may operate singly or in combination with other computing systems (e.g., where at least some the cross-sectional images 102 are stored remotely, and/or one or more modules described herein are associated with a cloud service accessed by computing system 100) to facilitate analysis of one or more lesions (or other findings) represented in one or more of the cross-sectional images 102. The computing system 100 may render the cross-sectional images 102 utilizing one or more hardware processors 108 (e.g., including a graphics processing unit (GPU)) for display on an I/O device interface 106, such as a monitor or other display screen. I/O device interface(s) 106 include any type of input or output device. Such devices include, but are not limited to, touch screens, displays, a mouse, a keyboard, a controller, head-mounted displays, microphones, speakers, sensors, sensor systems, and so forth. Any type of input or output device may be included among I/O device interface(s) 106, without limitation.

Utilizing I/O device interface(s) 106, the computing system may receive user input related to the analysis of the cross-sectional images 102 and one or more lesions or findings represented therein. For instance, a user may operate a mouse, keyboard, touchscreen, and/or other controller to select a pixel or pixel region of a cross-sectional image 102 associated with a lesion represented in the cross-sectional image. In some instances, the user may trace an outline, boundary, or shape of a lesion shown in a cross-sectional image. In other instances, the user may select, provide, and/or modify location information associated with a lesion/finding under analysis. In some instances, a user may provide vocal input to the system to facilitate generation of voice annotations of findings represented in the images. Additional examples and implementation details regarding user input received by the computing system 100 via I/O device interface(s) 106 to facilitate lesion analysis (e.g., lesion description, lesion identification/marking, longitudinal analysis, report generation, etc.) will be described in more detail hereafter.

In some instances, the computing system 100 utilizes image processing module(s) 110 to at least partially automate segmentation and/or measurement of lesions/structures identified in a cross-sectional image 102 to provide an estimated shape for the lesions/structures. For example, in response to receiving user input (e.g., via I/O device interface(s) 106) selecting a pixel region within a lesion shown in a cross-sectional image 102, the image processing module 110 may analyze the intensity of pixels within the pixel region. The image processing module 110 may determine that a boundary of the lesion exists where the contrast between pixels of the pixel region and pixels surrounding the pixel region exceeds a predetermined threshold level. The image processing module 110 may provide an estimated shape of the lesion based on the detected boundary, and the image processing module 110 may interpolate between boundary pixels to account for outlier boundary pixels and/or to provide a smooth lesion boundary.

In some instances, the image processing module 110 utilizes multiple different contrast threshold levels or edge sensitivity levels to determine multiple predicted shapes for the lesion, and the computing system 100 may allow or prompt the user to select a desired predicted shape as the segmentation for the lesion under analysis. In other instances, the threshold contrast or edge sensitivity is selectively modifiable by the user, and it will be appreciated that any other constraints may be applied to guide the segmentation process (e.g., shape, size, contour, angular, and/or curvature constraints). By way of example, in some implementations, the image processing module 110 may attempt to identify one or more (separate) pixel regions in neighboring cross-sectional images (e.g., at a higher or lower slice location or image number) that correspond to the pixel region of the lesion selected by the user and perform contrast analysis on the separate pixel regions of the neighboring images to determine predicted shapes for the separate pixel regions. The image processing module 110 may then utilize the shapes and/or sizes of the predicted shapes for the neighboring pixel regions as inputs for determining the predicted shape of lesion within the cross-sectional image under analysis.

As noted above, tracking target lesions over time is advantageous for obtaining accurate and precise evaluations of objective tumor response. To track a target lesion over multiple timepoints, a reviewer identifies a previously analyzed target lesion within a set of cross-sectional images captured at a timepoint subsequent to the timepoint at which the target lesion was previously analyzed. Similarly, tracking other findings on or within a patient's body over time can be advantageous for allowing medical practitioners to remain aware of potential changes in the patient's health.

In some embodiments, the image processing module 110 at least partially automates the identification of a later-timepoint cross-sectional image that includes the same lesion/finding that was analyzed in a previous-timepoint cross-sectional image. For example, the image processing module 110 may identify a predicted matching cross-sectional medical image (e.g., within a later-timepoint set of cross-sectional images) that corresponds to a previously captured cross-sectional image that included a lesion that was previously analyzed by image co-registration, feature matching, intensity similarity, and/or other techniques. The image processing module 110 may operate within various constraints to identify a predicted matching cross-sectional image, such as similarity thresholds or a search window within which to search for a matching image (e.g., a search window identified and/or centered based on a slice location of the previous-timepoint cross-sectional image). The image processing module 110 may expand the search window and/or selectively modify other inputs and/or constraints if no later-timepoint cross-sectional image meets or exceeds a predefined threshold of similarity to the previous-timepoint cross-sectional image containing the previously analyzed lesion.

The computing system 100, as shown in the example of FIG. 1, also includes machine learning module(s) 120, which may be configured to perform any of the operations, method acts, and/or functionalities disclosed herein. For example, machine learning module(s) 120 may comprise and/or utilize hardware components or computer-executable instructions operable to carry out function blocks and/or processing layers configured in the form of, by way of non-limiting example, single-layer neural networks, feed forward neural networks, radial basis function networks, deep feed-forward networks, recurrent neural networks, long-short term memory (LSTM) networks, gated recurrent units, autoencoder neural networks, variational autoencoders, denoising autoencoders, sparse autoencoders, Markov chains, Hopfield neural networks, Boltzmann machine networks, restricted Boltzmann machine networks, deep belief networks, deep convolutional networks (or convolutional neural networks), deconvolutional neural networks, deep convolutional inverse graphics networks, generative adversarial networks, liquid state machines, extreme learning machines, echo state networks, deep residual networks, Kohonen networks, support vector machines, neural Turing machines, and/or others.

As used herein, reference to any type of machine learning may include any type of artificial intelligence algorithm, device, structure, and/or architecture. Any amount or type of training data (e.g., datasets comprising cross-sectional medical images, control inputs provided by users, and/or, as ground truth, data corresponding to lesion analysis (e.g., lesion identification, segmentation, etc.) performed using the cross-sectional medical images) may be used (and/or later refined) to train a machine learning model to provide output for facilitating any of the disclosed operations.

In some instances, the computing system 100 utilizes machine learning module 120 to at least partially automate the localization of target lesions and/or non-target lesions. In some implementations, the machine learning module 120 is trained to identify location information for a lesion based on various input (e.g., type of cross-sectional image under analysis). For example, in some implementations, the computing system 100 provides the estimated shape (e.g., as determined above utilizing the image processing module 110, and/or as modified/indicated by user input) to the machine learning module 120 as input and causes the machine learning module to identify the location information for the analyzed lesion based on the estimated shape.

It should be noted that the machine learning module 120 may also be trained to receive other input for identifying location information for a lesion. In some instances, the machine learning module 120 receives as input a form of metadata indicative of an anatomical or organ location of the lesion. Such metadata may be associated with the particular cross-sectional image under review, the set of cross-sectional images 102 of which the particular cross-sectional image is a part, or even a user profile associated with the user performing the lesion analysis. For example, cross-sectional image or image set metadata may include an identifier of a slice location or image number or applicable anatomical location for the images captured (e.g., chest, abdomen, head, neck). Also, the user profile of the reviewer may indicate a radiology subspecialty (e.g., neuroradiology or thoracic radiology, which can include chest or abdomen subspecialties) which may inform the identification of the anatomical information associated with the lesion under analysis. In other instances, the machine learning module 120 receives as input pixel coordinates of user input directed at the lesion or of a pixel region within the lesion to guide the identification of the location information for the lesion. In yet other instances, the machine learning module analyzes structures neighboring the identified lesion and/or analyzes the cross-sectional image as a whole to identify the location information for the identified lesion.

At least some of the machine learning module(s) 120 may be configured as language modules, speech recognition modules, and/or natural language processing modules. For example, while viewing a cross-sectional image and/or structure represented therein, a user may produce a human voice signal (e.g., verbalization) that describes one or more aspects of the cross-sectional image and/or structure represented therein. The machine learning module(s) 120 may interpret the human voice signal to determine a voice annotation based on the human voice signal. A voice annotation may take on various forms and/or may be utilized in various ways. For example, a voice annotation may comprise a transcription of the human voice signal. In some instances, the voice annotation is used to select from a plurality of predefined attributes for the cross-sectional image and/or a structure represented therein. For example, the voice annotation may be parsed for keywords corresponding to anatomical location, lesion/finding type, etc., and such attributes may be selected for the structure represented in the cross-sectional image based on the voice annotation. A voice annotation may be used to modify the metadata of the cross-sectional image to bind the voice annotation to the cross-sectional image (e.g., to improve longitudinal analysis).

In some instances, voice annotation data, image data, labeling data, anatomical location data, and/or other types of data (or corrections made thereto from human users) may be used to refine and/or further train the machine learning module(s) 120.

As depicted in FIG. 1, the computing system 100 also includes data processing module(s) 114 and an export module 118. The data processing module 114, in some implementations, operates to determine or obtain lesion metrics associated with a lesion (e.g., a target lesion) under analysis or review. For instance, the data processing module 114 may, for one or more lesions at one or more timepoints, determine a major axis, a minor axis, and/or pixel area based on estimated lesion shape. The data processing module 114 may also perform calculations on lesion axes (e.g., comparing sums of the lengths of lesion axes over time) or other metrics to determine tumor response and/or disease progression based on predefined tumor response criteria as discussed above.

The data processing module 114 and/or the export module 118, in some implementations, is also responsible for organizing and/or storing data/information associated with analyzed lesions. For example, the data processing module 114 may store and/or copy within one or more lists or databases the predicted shape, axes (major and/or minor), slice location or cross-sectional image number, location information, key images (e.g., images showing close-up views of a lesion), voice annotations, or any combinations or representations thereof associated with any number of lesions at any number of timepoints. For example, in some embodiments, any of the foregoing types of data associated with the lesions become stored in association with and/or within the cross-sectional images themselves (e.g., as metadata or as a modified version of the cross-sectional images with data implemented or embedded therein). In some instances, the data/information become stored within hardware storage device(s) 112, remote storage database system(s) 124 (e.g., within a cloud server), and/or on one or more remote computing device(s) 130a, 130b, 130c (via network 128).

In some implementations, and as will be discussed hereafter, the data processing module 114 and/or export module 118 may compile or generate reports based on any of the data/information described herein for oncological and/or patient review. Such reports may comprise one or more results and/or output of lesion analysis performed by one or more than one physician.

It will be appreciated that the computing devices 130a, 130b, 130c can have any or all of the components and modules described above for the general computing system 100. In some instances, the computing system 100 can include the workstation of a physician reviewer. Alternatively, the computing system 100 can include a server for hosting or facilitating user interaction with cross-sectional images and/or computer-executable instructions (e.g., in the form of software or a SaaS platform) for standardizing target lesion identification and selection within cross-sectional images, as described herein. Similarly, the computing devices 130a, 130b, 130c can represent the workstations of other reviewers, or the computing devices 130a, 130b, 130c can be user profiles or virtual instances of computing system 100. For instance, different physician reviewers with different specialties and/or subspecialties may perform lesion analysis on different subsets of one or more sets of cross-sectional medical images, and such analysis may be performed at the same or different times. Such analysis by multiple reviewing physicians may be compiled into a composite report by any of the computing systems/devices described herein.

Regardless of the physical and/or virtual organization of the computing system 100 and/or the associated computing devices 130a, 130b, 130c, embodiments of the present disclosure enable cross-sectional images to be received and/or viewed at any of the foregoing system/devices 100, 130a, 130b, 130c. The ellipsis shown in FIG. 1 indicate that any number of computing systems (e.g., 1, 2, or more than 3) may be in communication with computing system 100 via network 128.

Example Techniques for Facilitating Image Finding Analysis

The following discussion refers to FIGS. 2-19 and provides additional details, examples, and implementations related to systems and methods for facilitating analysis of lesions in cross-sectional medical images. It will be appreciated that the contents of the accompanying Figures are not mutually exclusive. For instance, any feature, component, or embodiment shown in any one of the accompanying Figures may be combined with one or more features, components, or embodiments shown in any other accompanying Figure.

Figure 2:
FIG. 2 illustrates an example user interface presenting a set of cross-sectional medical images in navigable form.

FIG. 2 illustrates an example user interface 200 presenting a set of cross-sectional medical images in navigable form. The user interface 200 may be presented utilizing a computing system 100 as described hereinabove (e.g., utilizing hardware processor(s) 108, hardware storage device(s) 112, I/O device interface(s) 106, etc.). As shown, the user interface 200 presents image 202, which is part of a set of 268 images (i.e., FIG. 2 indicates that image 202 is image slice 91 of the 268 image slices). The set of images comprises a set of cross-sectional medical images (e.g., CT images) obtained for a patient at a particular timepoint.

The user interface 200 includes a cursor 204 representative of a user-operated controller (shown in FIG. 2 as a mouse cursor) and/or various controls (e.g., buttons of a mouse that controls the mouse cursor) for performing various functions. Other controls (e.g., I/O device interface(s) 106) may be operable for providing user input within the user interface not shown in FIG. 2 (e.g., a microphone, keyboard, or other physical controls that are operable by the user to interface with the system).

Figure 3:
FIG. 3 illustrates an example of user input directed to a target lesion represented in a cross-sectional medical image.

Utilizing such controls, a user may navigate through the set of images to search for findings to analyze (e.g., to determine objective tumor response and/or otherwise assess the patient's health and/or bodily response to a treatment). By way of non-limiting example, a user may scroll a mouse wheel, press keyboard buttons, and/or click on elements presented in the user interface to navigate from one image of the set of images to another. For instance, FIG. 3 illustrates the user interface 200 displaying a different image 302 from the same set of 268 images of FIG. 2 (i.e., FIG. 3 indicates that image 302 is image slice 93 of the 268 image slices).

Once the user has navigated to an image that depicts a structure for analysis (e.g., a lesion such as a mass or lymph node, a metastasis, or other bodily structure), the user may interact with the user interface 200 to analyze the structure. In some implementations, structures may be analyzed as target lesions or non-target lesions (e.g., according to a tumor response criterion), or other findings. FIG. 3 illustrates the cursor 204 positioned over a lesion in the liver of the patient represented in the image 302. A user may provide user input directed to the portion of the image 302 corresponding to the liver lesion (e.g., by clicking or otherwise selecting the portion of the image 302) to initiate and/or trigger analysis of the liver lesion. In some implementations, analysis may be initiated and/or triggered using other types of user input (e.g., by the user drawing a bounding box or boundary around the lesion). In the example of FIG. 3, the liver lesion is analyzed as a target lesion.

Figure 4:
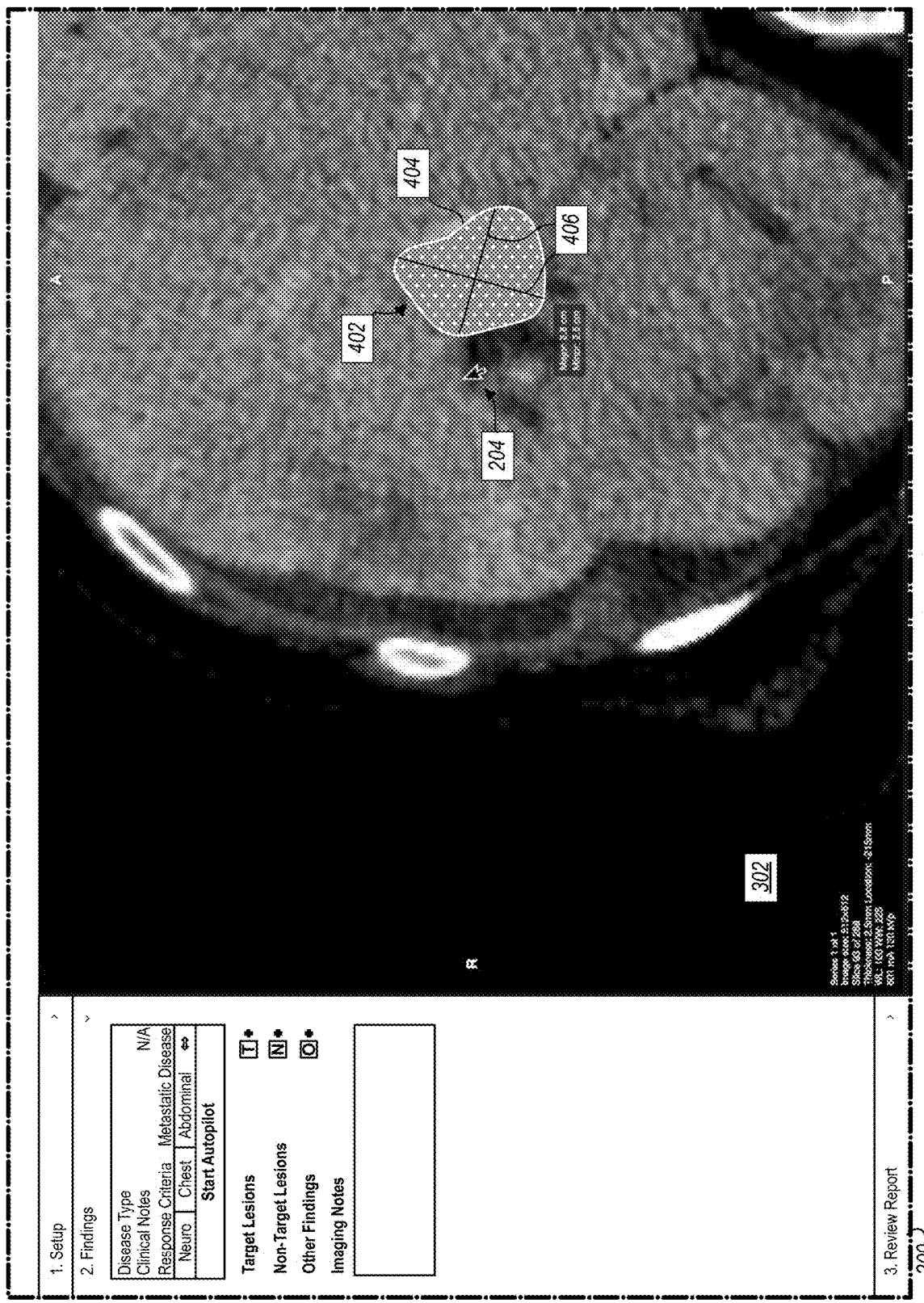
FIG. 4 illustrates an example of a label placed over the target lesion of FIG. 3.

FIG. 4 illustrates aspects of lesion analysis related to lesion segmentation (e.g., determining a region of interest (ROI) for the lesion). In particular, FIG. 4 illustrates the image 302 from FIG. 3 and illustrates a label 402 generated for the liver lesion represented in the image 302. The label 402 of the example shown in FIG. 4 includes various components. In particular, FIG. 4 shows the label 402 as including an estimated segmentation 404 (e.g., estimated shape, or ROI) for the liver lesion. FIG. 4 also depicts the label 402 as including axes 406 determined for the liver lesion (e.g., based on the estimated segmentation 404). As noted above, such attributes for the liver lesion (captured by the label 402) may be automatically determined using machine learning module(s) 120 (or other artificial intelligence (AI) module(s)).

Figure 5:
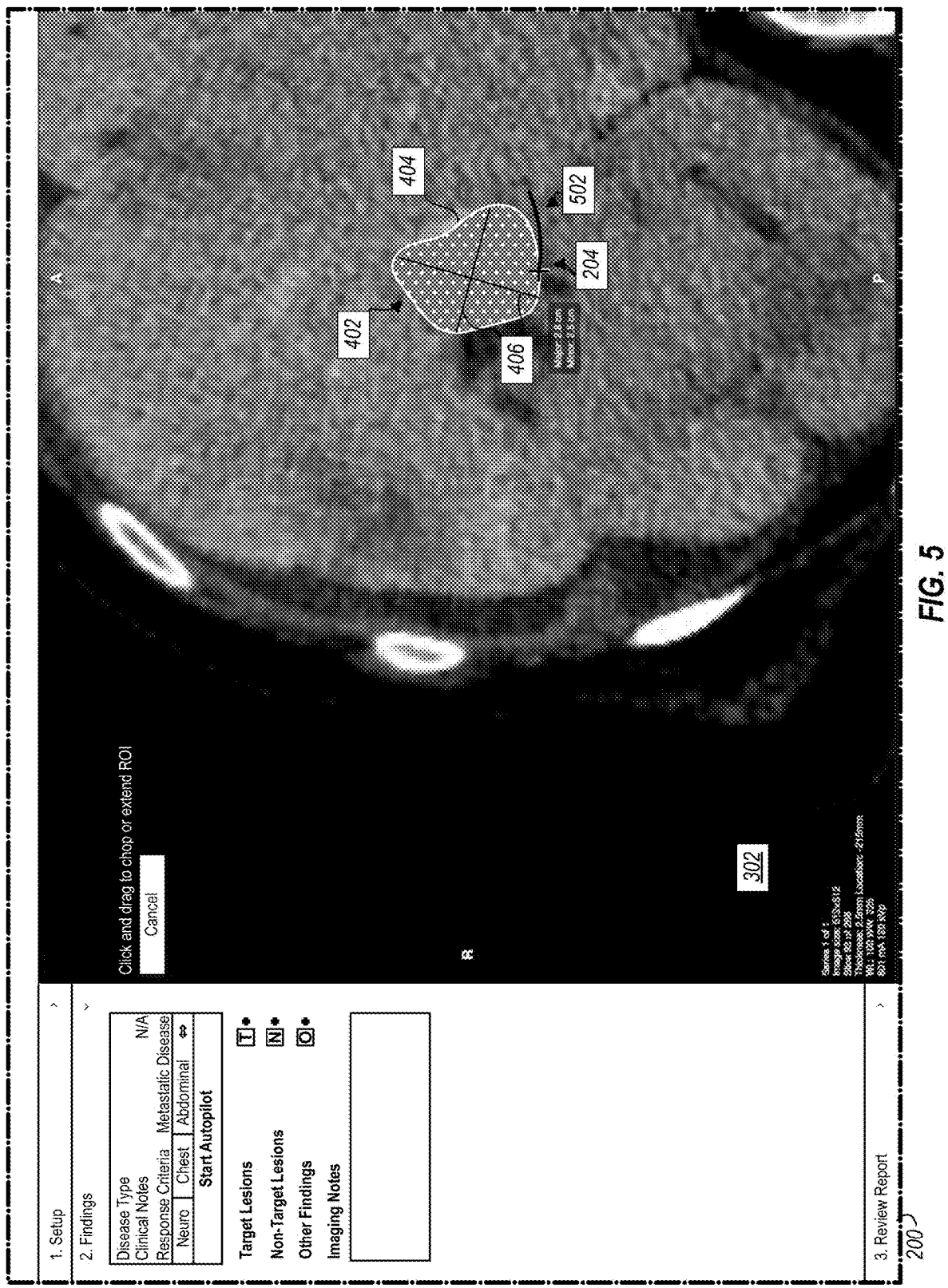
FIG. 5 illustrates an example of user modification of the label of FIG. 4.
Figure 6:
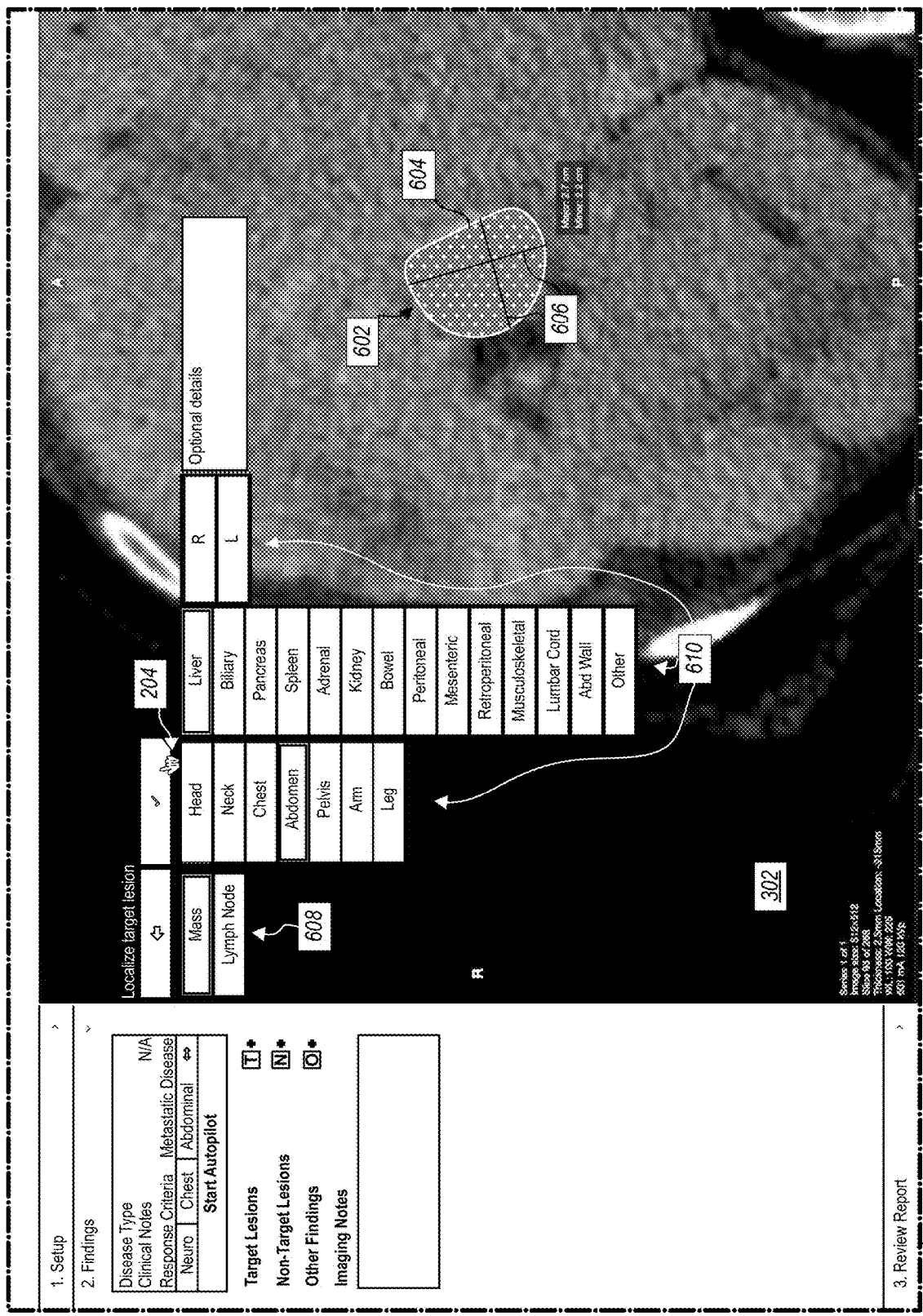
FIGS. 6 and 7 illustrate an example of determining lesion type and anatomical information for the target lesion of FIGS. 3,4, and 5.

In some implementations, the estimated segmentation 404 and/or axes 406 of the label 402 are selectively modifiable by the user. For instance, FIG. 5 illustrates an example of user modification of the label 402 of FIG. 4. In particular, FIG. 5 illustrates a user providing input 502 (guided by the cursor 204) to modify the estimated segmentation 404. For example, such input 502 may redraw, chop, extend, and/or otherwise modify the estimated segmentation 404 to generate updated segmentation 604 and/or updated axes 606 (as illustrated in FIG. 6 as part of an updated label 602). User modifications to lesion labels and/or segmentation may be used to further train or refine the AI module(s) used to generate subsequent estimated segmentations/measurements.

In some instances, the lesion/structure attributes (e.g., segmentation, shape, axis length) represented in the label 602 (or 402) may be used to determine objective tumor response and/or otherwise assess the progression of the liver lesion. In some instances, a label 602 (or 402) is associated with additional or alternative lesion attributes. For example, selection of the portion of the image 302 corresponding to the liver lesion (and/or user input defining, modifying, or accepting a lesion segmentation and/or lesion measurements) may trigger automatic identification of a lesion type 608 and/or anatomical location information 610. In the example shown in FIG. 6, based on the updated segmentation 604, a lesion type 608 corresponding to "mass" is automatically selected for the target liver lesion (rather than "lymph node"). Furthermore, FIG. 6 illustrates automatically identified anatomical location information 610 for the target lesion indicating that the lesion is within the liver of the abdomen of the patient. As indicated above, lesion type 608 and/or anatomical location information 610 may be automatically obtained using machine learning module(s) 120 trained to determine such output in response to input image data (e.g., segmentation data, pixel coordinate data, image metadata, etc.). In some implementations, as shown in FIG. 6, the lesion type 608 and/or anatomical location information 610 are displayed contemporaneous with presentation of the structure/lesion of the image 302.

FIG. 6 furthermore illustrates that, in some instances, users may modify the lesion type 608 and/or the anatomical location information 610. For example, FIG. 6 illustrates the options provided for lesion type 608 and/or anatomical location information 610 implemented as selectable buttons, which the user may select to modify the lesion the lesion type 608 and/or anatomical location information 610.

Figure 7:
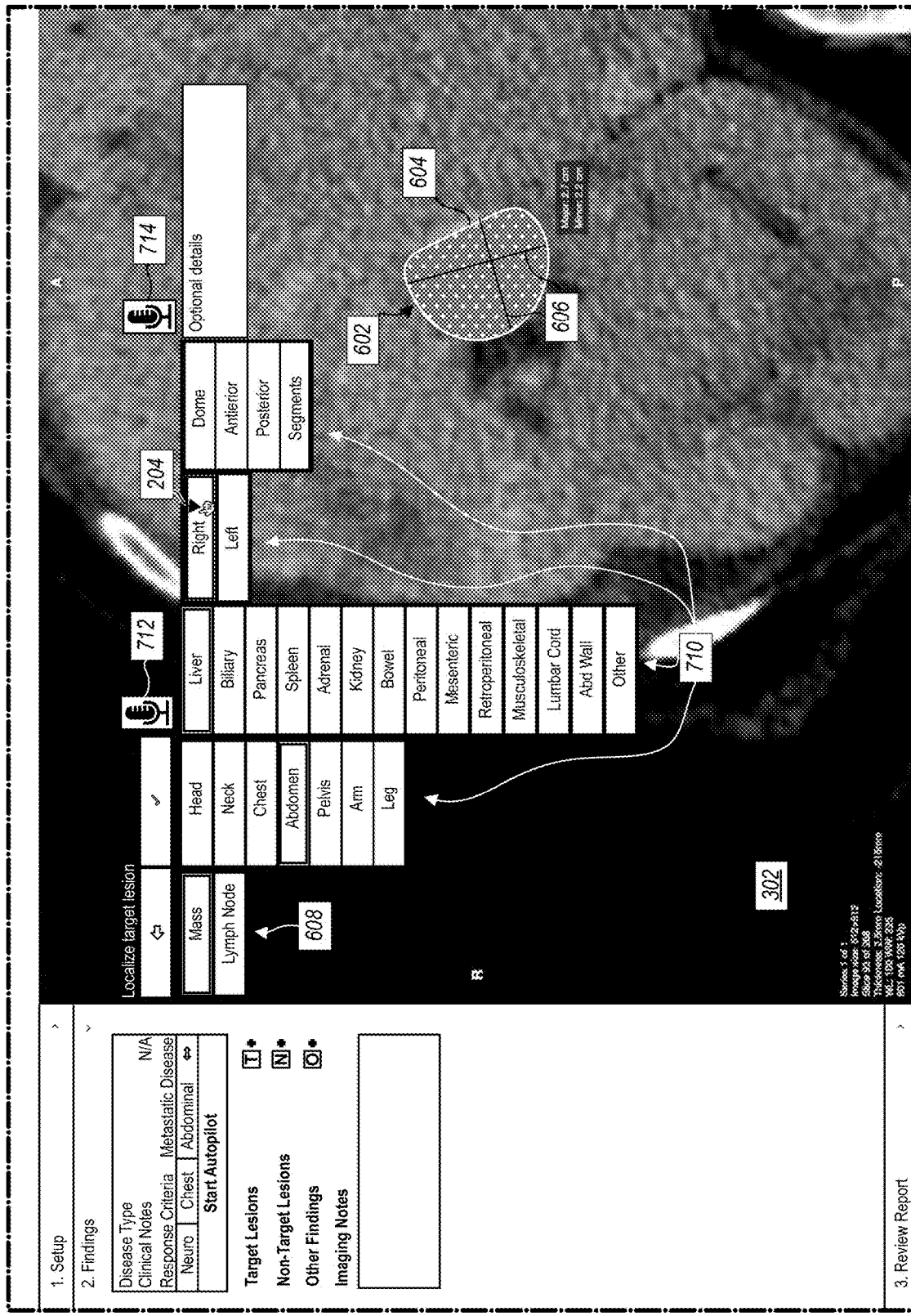

In some instances, a system refrains from automatically estimating at least some aspects of lesion anatomical location information 610 (or lesion type 608), such as where an estimated output is associated with a level of confidence that fails to satisfy a threshold. FIG. 6 illustrates an example in which a system refrains from estimating whether the live lesion is in a right or left lobe of the liver, while still presenting "right" and "left" selectable elements to allow the user to further specify such aspects of the target liver lesion if desired. FIG. 7 shows an example where the user has provided input specifying that the liver lesion is in the right lobe of the liver and where the user is prompted to provide additional specificity as to the updated anatomical location information 710 for the target liver lesion.

User input selecting or modifying aspects of structure/lesion type and/or anatomical location information may be provided in various ways. For example, FIG. 7 illustrates that user input provided via a user controller (e.g., a mouse (guided by cursor 204), keyboard input, etc.) may be used to select one or more aspects of structure/lesion type and/or anatomical location information.

In some implementations, user input selecting or modifying aspects of structure/lesion type and/or anatomical location information can be provided in the form of voice annotations. For example, FIG. 7 illustrates a microphone icon 712 which may be selectable by the user to activate a dictation tool for capturing human voice signals uttered by the user (e.g., via a microphone or other I/O device interface(s) 106). The system may use the human voice signals to generate the voice annotation (e.g., utilizing machine learning module(s) 120). For instance, the system may detect or recognize keywords within the user utterances corresponding to structure/lesion types (e.g., mass, lymph node, etc.) and/or anatomical location information and may utilize such recognized keywords to select or modify the lesion type 608 lesion anatomical location information 610/710. Such functionality may advantageously allow the user to avoid manually entering such information (e.g., allowing users to avoid traversing multi-layered lists or trees of selectable elements to arrive at a desired location or type designation).

Figure 8:
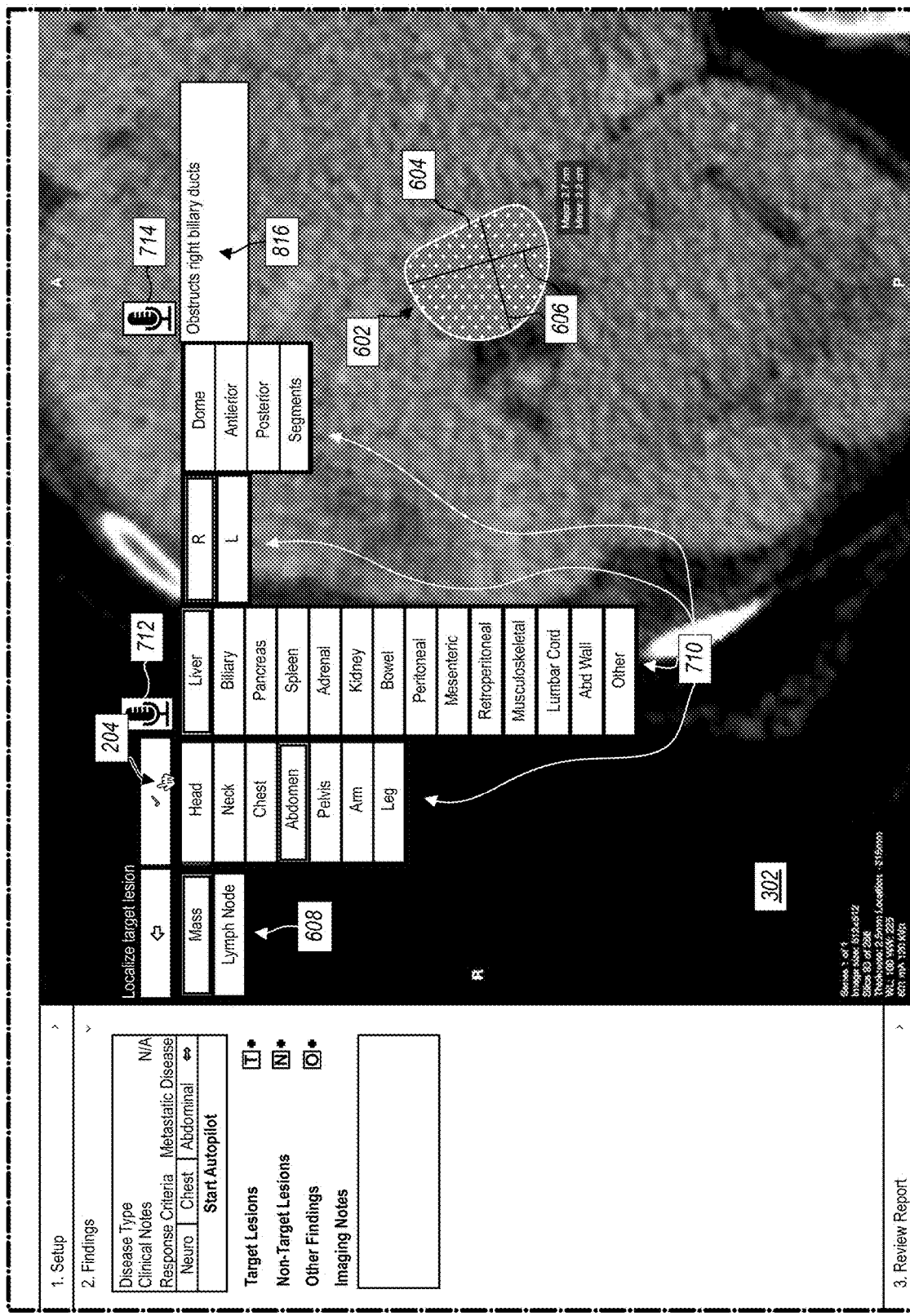
FIG. 8 illustrates an example of obtaining a voice annotation of the target lesion of FIGS. 3-7.

In some implementations, a voice annotation is additionally or alternatively usable to capture a user description of details of a structure/lesion and/or other observations about a patient (or set of images representing a patient). For example, FIG. 7 illustrates an additional microphone icon 714 that a user may select to activate a dictation tool for capturing human voice signals. The human voice signals may be transcribed (e.g., via machine learning module(s) 120) to form a transcription 816 (shown in FIG. 8). The transcription 816 shown in FIG. 8 indicates that the target lesion "Obstructs [the] right biliary ducts," which captures an observation made by the user analyzing the target lesion. FIG. 8 illustrates an example in which the transcription 816 is displayed contemporaneous with at least a portion of the image 302 (e.g., the portion of the image 302 that depicts the target lesion), which may allow the user to easily detect dictation errors without removing their focus from the lesion analysis task at hand. The transcription 816 is shown in FIG. 8 as overlaid on the image 302, but other configurations are within the scope of the present disclosure (e.g., the transcription 816 may be displayed adjacent to the depiction of the image 302). In some instances, the transcription 816 is displayed contemporaneous with the lesion type 608 and/or the anatomical location information 610/710 to allow the user to observe additional relevant lesion information as the user dictates observations about the lesion/structure. Such functionality may allow users to advantageously obtain and/or view voice annotations within the same user interface 200 or software application that facilitates analysis of lesions/structures present within images, which may improve user efficiency and/or accuracy when recording such dictations (and/or when comparing recorded analysis to subsequent images, see FIGS. 17-19).

One will appreciate, in view of the present disclosure that the particular depictions of selectable elements for activating dictation tools (e.g., microphone icons 712 and 714) in FIGS. 7 and 8 are provided by way of example only. For example, selectable elements for activating a dictation tool may be provided at any suitable location on a user interface.

Such selectable elements may be overlaid on the image 302 for ready access and/or displayed contemporaneous with anatomic location information, lesion type, a representation of the lesion/structure, etc. In some implementations, the voice annotation is obtained (e.g., via a dictation tool) contemporaneous with presentation of at least a portion of the image 302 (e.g., the portion of the image 302 that depicts the target liver lesion), which may allow users to conveniently provide verbal descriptions of structures present in images while viewing the images. As noted above, user dictation may be displayed in proximity to the image 302 to allow users to readily detect and/or correct dictation errors. User corrections of dictation errors may be utilized to further train AI module(s) for facilitating speech recognition.

In some instances, at least some user inputs described hereinabove for performing other functions may additionally be operable to activate a dictation tool (e.g., selection a portion of the image 302, modifying or accepting a lesion segmentation and/or measurement, selecting selectable elements related to identification of lesion type and/or anatomical location, etc.). Other types of input for activating a dictation tool are within the scope of the present disclosure, such as by touching or pressing a physical controller (e.g., one or more keyboard buttons), providing gesture input, providing gaze input, providing vocal keyword input (e.g., a vocal keyword for triggering detection of additional utterances), combinations thereof, and/or others.

In view of the foregoing, a voice annotation may be generated based on detected human voice signals and may comprise or indicate one or more of structure/lesion type, anatomical location information, and/or observations/details related to the structure/lesion. Voice annotations may be bound to one or more aspects of an image (e.g., image 302), such as by modifying metadata of the image based on the voice annotations. For example, a user may provide input to finalize structure/lesion attributes/characteristics (e.g., segmentation, measurements, voice annotations, type, anatomical location information, etc.), as depicted in FIG. 8 by the cursor 204 directed to a check mark button in FIG. 8. Responsive to such input, a system may create or modify metadata of the image 302 to bind the structure/lesion attributes/characteristics to the image 302.

Figure 9:
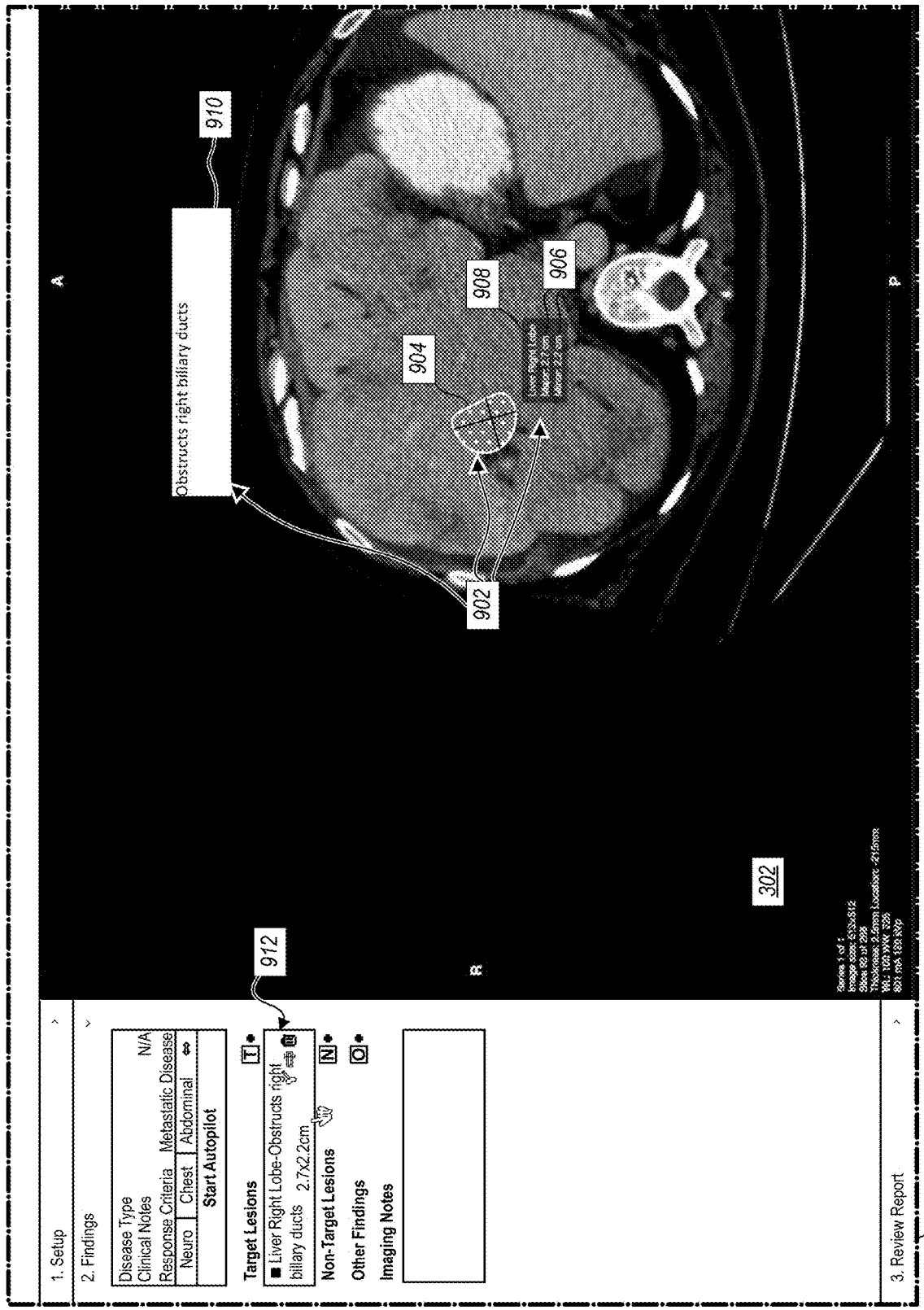
FIG. 9 illustrates a conceptual representation of binding the voice annotation of FIG. 8 to the cross-sectional medical image of FIGS. 3-8.

FIG. 9 illustrates a conceptual representation of lesion attributes/characteristics 902 bound to the image 302. As depicted in FIG. 9, the lesion attributes/characteristics 902 include lesion segmentation 904 and axis measurements 906 (e.g., as represented by the label 602 and/or 402 discussed above). FIG. 9 also shows the lesion attributes/characteristics 902 as including anatomical location information 908 and a dictation 910 (which may be at least partially obtained as voice annotations). Lesion attributes/characteristics 902 may comprise any selection of the foregoing and/or other attributes/characteristics. In some instances, the binding of the lesion attributes/characteristics to the image 302 causes display of the lesion attributes/characteristics 902 to be triggered or triggerable when the image 302 is viewed in a user interface (e.g., user interface 200). For example, as shown in FIG. 9, at least some of the lesion attributes/characteristics 902 may surface when a user navigates to the image 302 within the user interface 200. In some implementations, as shown in FIG. 9, a summary of at least some lesion attributes/characteristics found in metadata of images within the set of images presented on the user interface 200 is displayed along with an image viewer for viewing images. For example, FIG. 9 illustrates summary element 912, which includes representations of at least some of the lesion attributes/characteristics 902 of the target liver lesion discussed above. In some instances, the summary element 912 comprises a selectable element that, when selected, facilitates navigation directly to the image 302 (and/or display of at least some of the lesion attributes/characteristics 902 represented in the metadata of the image 302).

One will appreciate, in view of the present disclosure, that metadata for images (and/or sets of images) may be stored in any suitable format and/or organizational structure. For example, a label (e.g., label 602 or 402) and a voice annotation may be stored as separate data objects or as part of the same data object.

Figure 10:
FIG. 10 illustrates an example of user input directed to a finding represented in a cross-sectional medical image.
Figure 11:
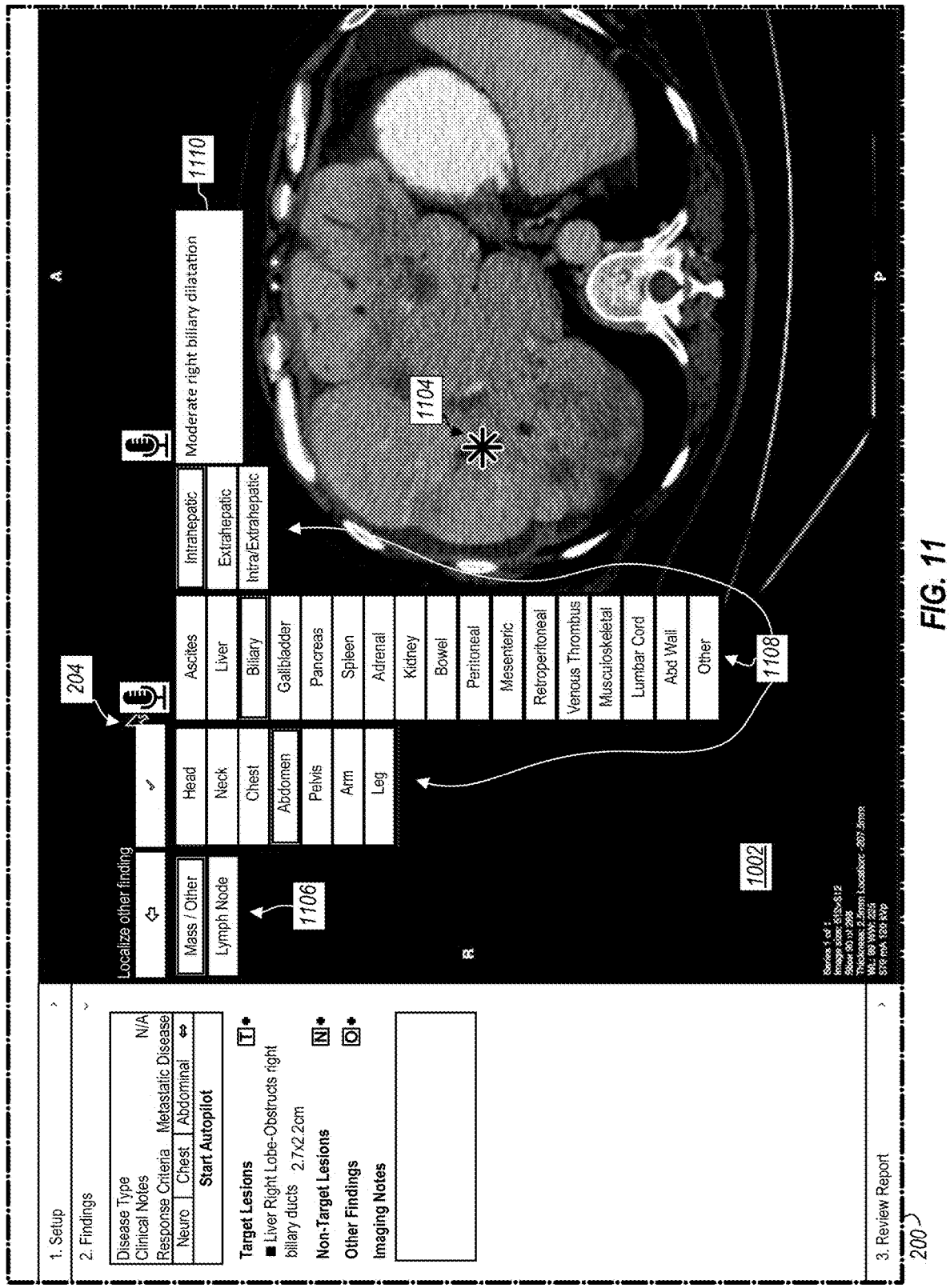
FIG. 11 illustrates an example of a label, anatomical information, and a voice annotation for the other finding of FIG. 10.

Although FIGS. 2-9 have focused on an example in which the structure under analysis is a target lesion, the principles discussed herein may be applied to other types of structures analyzed for various purposes. For instance, FIGS. 10-15 illustrate examples further analysis of other findings (e.g., structures that are not analyzed as target lesions or non-target lesions). FIG. 10 shows an example of a user providing input (guided by cursor 204) at the user interface 200 directed to a portion of an image 1002 corresponding to a biliary dilatation of the patient. FIG. 11 illustrates a label 1104 placed in association with the biliary dilatation based on the user input of FIG. 10. In view of the label 1104 of FIG. 11, a label according to the present disclosure may comprise or omit segmentation and/or measurements.

Figure 12:
FIG. 12 illustrates a conceptual representation of binding the voice annotation of FIG. 11 to the cross-sectional medical image of FIGS. 10 and 11.

FIG. 11 furthermore illustrates finding type 1106 and anatomical location information 1108 for the biliary dilatation, which may be obtained via user input (e.g., manual input and/or voice annotations) and/or utilizing AI module(s). FIG. 11 furthermore illustrates a voice annotation 1110 obtained based on user vocalization, which describes the other finding as a "Moderate right biliary dilatation." FIG. 12 illustrates a representation of the label 1104 and the voice annotation 1110 bound to the biliary dilatation represented in the image 1002, wherein the binding causes the metadata of the image 1002 to be modified based on the label 1104 and/or the voice annotation 1110 (e.g., such that the label 1104 and/or the voice annotation 1110 become visible when the image 1002 is navigated to within the user interface 200). FIG. 12 further depicts information from the metadata of the image 1002 represented as a selectable summary element 1202 that facilitates rapid navigation to the image 1002 and/or display of information associated therewith.

Figure 13:
FIGS. 13-15 illustrate an additional example of obtaining a label, anatomical information, and a voice annotation for a finding of a cross-sectional medical image and binding the voice annotation to the cross-sectional medical image.
Figure 14:
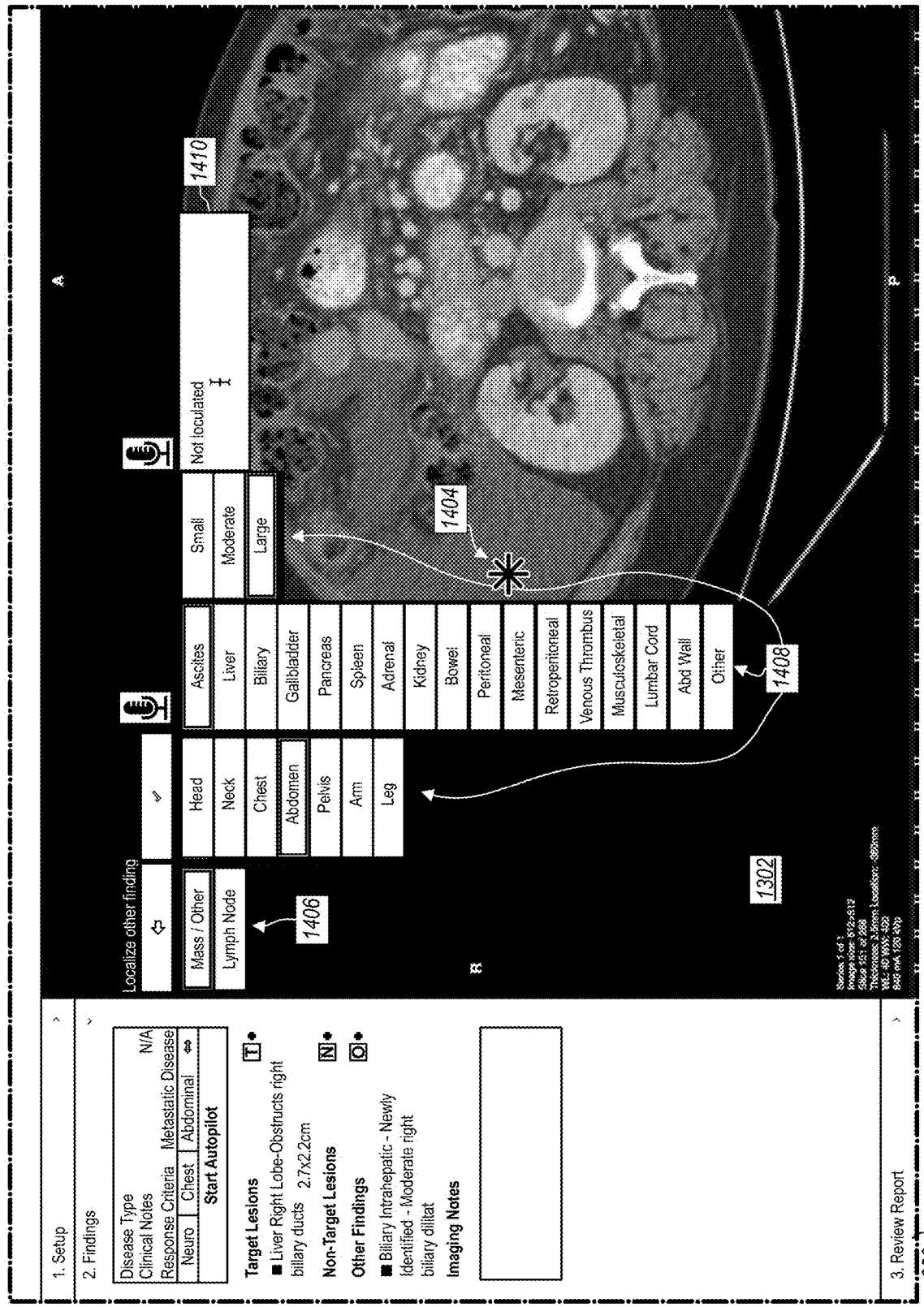

Similarly, FIG. 13 shows an example of a user providing input (guided by cursor 204) at the user interface 200 directed to a portion of an image 1302 corresponding to an ascites of the patient. FIG. 14 illustrates a label 1404 placed in association with the ascites based on the user input of FIG. 13.

Figure 15:
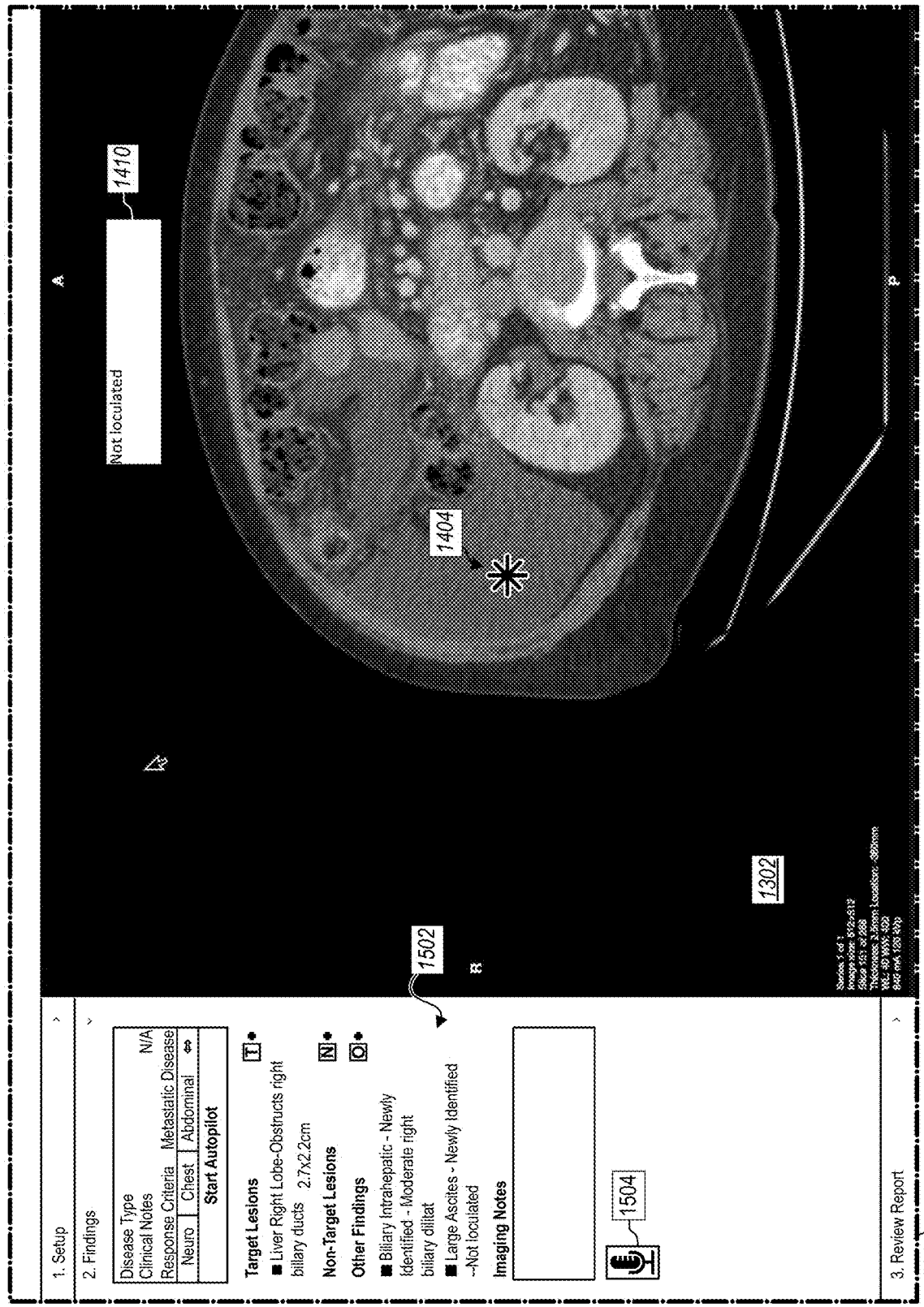

FIG. 14 furthermore illustrates finding type 1406 and anatomical location information 1408 for the ascites, which may be obtained via user input (e.g., manual input and/or voice annotations) and/or utilizing AI module(s). FIG. 14 furthermore illustrates a voice annotation 1410 obtained based on user vocalization, which describes the other finding as a "Not loculated." FIG. 15 illustrates a representation of the label 1404 and the voice annotation 1410 bound to the ascites represented in the image 1302, wherein the binding causes the metadata of the image 1302 to be modified based on the label 1404 and/or the voice annotation 1410 (e.g., such that the label 1404 and/or the voice annotation 1410 become visible when the image 1302 is navigated to within the user interface 200). FIG. 15 further depicts information from the metadata of the image 1302 represented as a selectable summary element 1502 that facilitates rapid navigation to the image 1302 and/or display of information associated therewith.

FIG. 15 furthermore illustrates an additional microphone icon 1504, which may be selectable by a user to activate a dictation tool for obtaining voice annotations that are associated with a set of images generally (a dictation tool may be activated for such a purpose in other ways, as described herein). Such voice annotations may be utilized to modify the metadata of the set of images generally (rather than for specific image slices).

Furthermore, it should be noted that voice annotations (e.g., transcribing user vocalizations) may be obtained for particular image slices (e.g., an image slice currently displayed within the user interface 200) without first obtaining segmentation, measurement information, structure type, anatomical location information, etc. Such voice annotations may be utilized to modify the metadata for the corresponding image slice.

In some instances, metadata for images (and/or sets of images) may be used to generate a report that compiles information for structures analyzed within a set of images. For example, FIG. 16 illustrates an example report 1602 that includes voice annotations 1604 for analyzed lesions. In some instances, the voice annotations 1604 are obtained by accessing the metadata stored for the various images (e.g., images 302, 1002, 1302) of the set of images. Such a report 1602 may provide users with a useful summary for ascertaining the medical status of a patient and/or the patient's bodily response to a treatment. It will be appreciated, in view of the present disclosure, that a report may implement information from a number of different image sets associated with different timepoints (e.g., to facilitate longitudinal analysis of lesions to determine objective tumor response).

Figure 17:
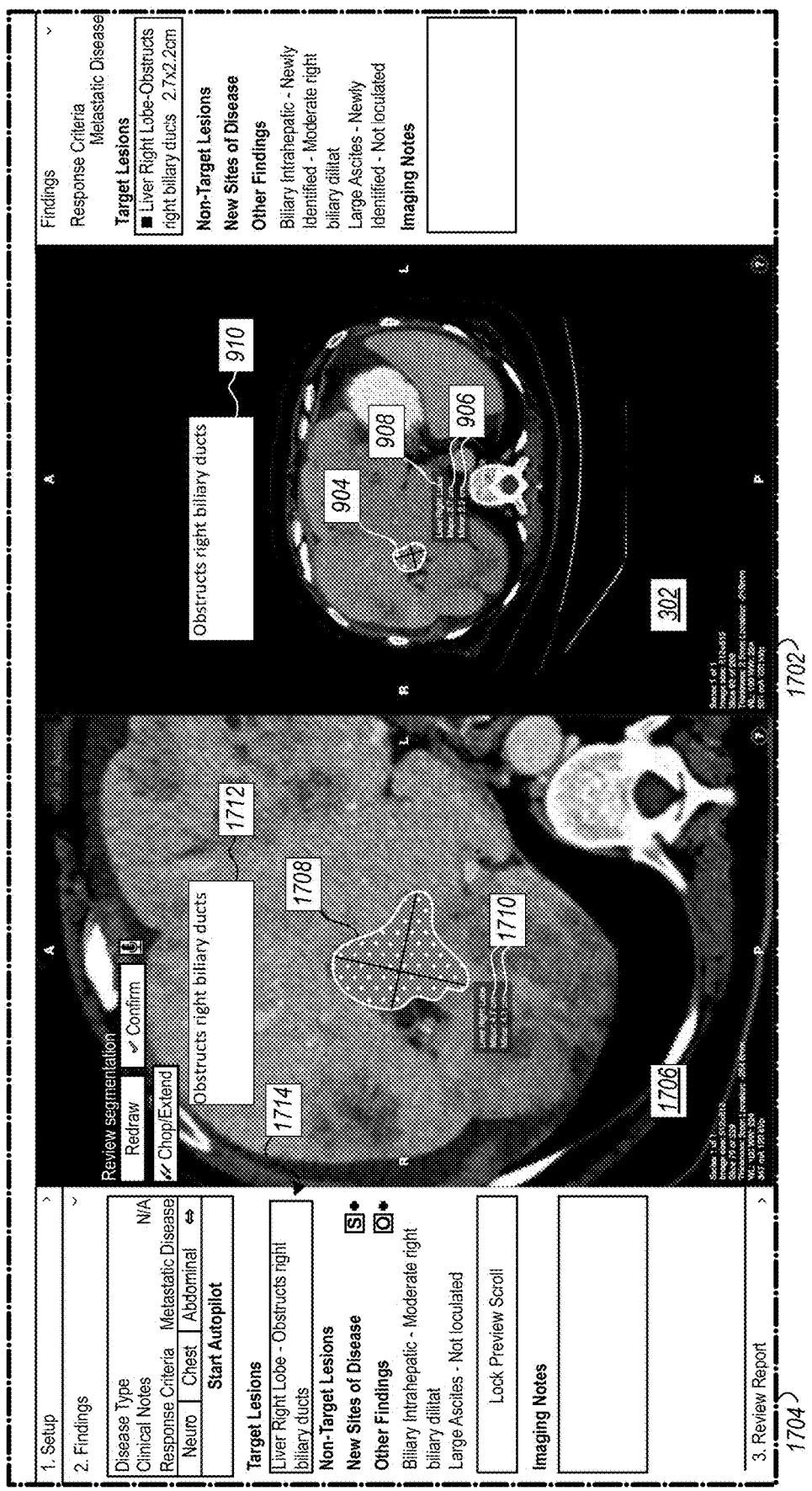
FIG. 17 illustrates an example of analyzing the target lesion of FIGS. 3-9 in a corresponding subsequent-timepoint cross-sectional medical image.

As indicated hereinabove, analysis performed on a set of images associated with one timepoint may be used to assist in analysis of a set of images associated with a different timepoint. Such functionality may be useful, for example, to facilitate longitudinal analysis of target lesions, non-target lesions, and/or other findings to determine objective tumor response (and/or other conclusions). For example, FIG. 17 illustrates an example of analyzing the target lesion of FIGS. 3-9 in a corresponding subsequent-timepoint cross-sectional medical image. In particular, FIG. 17 illustrates a first user interface 1702 presenting a first set of images (e.g., the 268 image slices shown on the right side of FIG. 17) of the patient from which various findings were analyzed as discussed with reference to FIGS. 3-9. This first set of images may be associated with a first timepoint at which the patient's body was scanned. The user interface 1702 of FIG. 17 depicts image 302 (image slice 93 of the 268 image slices) of the first set of images and depicts representations of the lesion attributes/characteristics represented in the metadata associated with image 302 (e.g., the lesion segmentation 904, the axis measurements 906, the anatomical location information 908, the dictation 910, etc.). In this regard, metadata describing one or more aspects of a structure/lesion represented in an image may be obtained and presented contemporaneous with the structure shown in the image.

FIG. 17 also illustrates a second user interface 1704 presenting a second set of images (e.g., the 229 image slices shown on the left side of FIG. 17) which captures a scan of the same patient at a different (e.g., subsequent) timepoint. Using the structures analyzed in the first set of images as a baseline, a user may analyze the second set of images to assess changes in the structures to, for example, assess objective tumor response. One will appreciate, in view of the present disclosure, that the second user interface 1704 and the first user interface 1702 may be provided as different parts of the same user interface or as separate user interfaces that are executed or displayed in parallel.

FIG. 17 shows the second user interface 1704 displaying an image 1706 of the second set of images (image slice 76 of the 229 image slices). Images 1706 and 302 may be displayed contemporaneous with one another to facilitate accurate analysis of structures across timepoints. For example, a user may observe the lesion/structure represented in image 302 from an earlier timepoint and may search or scroll through the second set of images to find an image slice that depicts the same lesion/structure from a later timepoint. In some instances, the user's identification of an image in the second set of images that depicts the same lesion/structure is at least partially assisted by AI module(s) and/or other image processing techniques (e.g., image co-registration).

As is evident from FIG. 17, systems of the present disclosure may be configured to display lesion characteristics/attributes of a lesion in a first timepoint (e.g., the lesion segmentation 904, the axis measurements 906, the anatomical location information 908, the dictation 910, etc.) contemporaneous with display of a corresponding representation of the same lesion in a second timepoint (e.g., depicted in image 1706). Such functionality may assist users in readily evaluating the presence and/or status of a lesion/structure in a subsequent-timepoint image.

Image 1706 of FIG. 17 corresponds to an image that depicts the same liver lesion represented in image 302, but at a different (e.g., later) timepoint. FIG. 17 illustrates segmentation 1708 and axis measurements 1710 obtained for the liver lesion as depicted in image 1706. The segmentation 1708 and/or the axis measurements 1710 may be obtained using techniques described hereinabove with reference to the segmentation of the liver lesion in image 302 (see FIGS. 3-9).

As shown in FIG. 17, a first voice annotation (e.g., dictation 910) associated with a first image (e.g., image 302) is presented contemporaneous with the second image (e.g., image 1706), which may allow the first voice annotation to influence the user's analysis of the second image and/or structures represented therein. The first voice annotation may be visually displayed or emitted as an audio signal contemporaneous with the second image. For example, dictation 910 indicates that the liver lesion (at the first timepoint) "Obstructs [the] right biliary ducts".

In some instances, a user may determine that a previous dictation/description obtained in association with a first timepoint is still applicable or relevant to the structure as represented at a second timepoint. Thus, in the example shown in FIG. 17, a user may cause the dictation 910 to be used to modify metadata of image 1706 to associate the dictation 910 (or voice annotation) with image 1706 (and/or structures represented therein). By way of non-limiting example, a user may select the representation of the dictation 910 to cause the dictation 910 to become associated with the image 1706, or the dictation 910 may be automatically associated with the image 1706 by default (e.g., upon determining that image 1706 depicts a lesion that corresponds to the lesion depicted in image 302) while still allowing the user to subsequently modify voice annotations associated with the image 1706. FIG. 17 illustrates a dictation 1712 for the image 1706 that mirrors the dictation 910, and FIG. 17 illustrates a summary element 1714 for depicting lesion metadata of the image 1706 that incorporates the dictation 1712.

Figure 18:
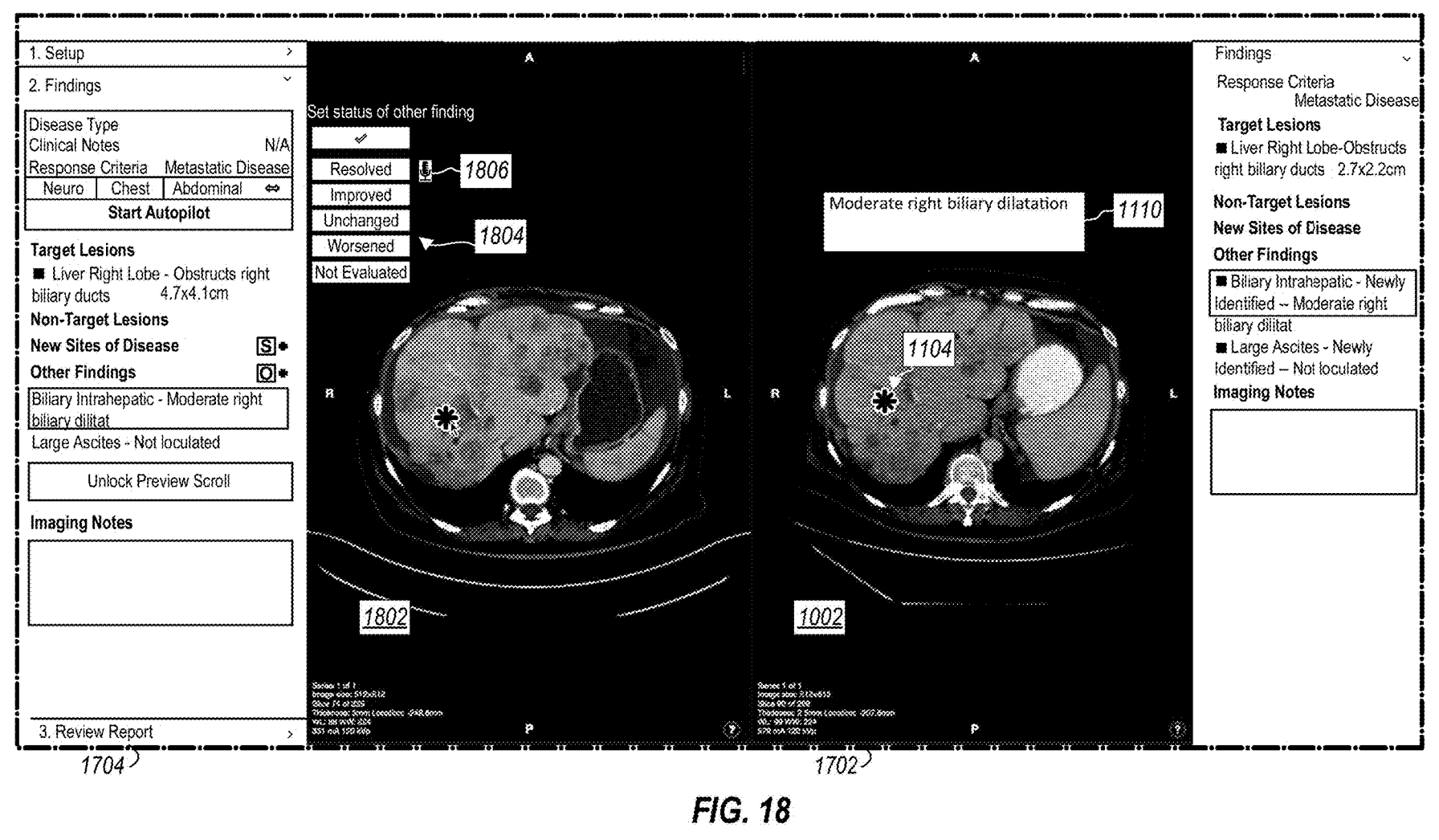

In some instances, a user may determine that a status of a structure represented in a previous-timepoint image has changed as indicated by one or more subsequent-timepoint images. For example, FIG. 18 illustrates longitudinal analysis of the biliary dilatation discussed hereinabove with reference to FIGS. 10-12. FIG. 18 illustrates the first user interface 1702 depicting image 1002 and attributes/characteristics of the finding (biliary dilatation) previously labeled in image 1002 (e.g., the label 1104, the voice annotation 1110, etc.). FIG. 18 also illustrates the second user interface 1704 illustrating image 1802 of the second set of images (e.g., image slice 99 of the 229 image slices), which depicts the same biliary dilatation at the second (e.g., later) timepoint. FIG. 18 illustrates various selectable status indicators 1804 allowing the user to indicate a status of the biliary dilatation as represented at the second timepoint (e.g., in image 1802). For example, the example status indicators 1804 of FIG. 18 include selectable elements of "Resolved", "Improved", "Unchanged", "Worsened", and "Not Evaluated", which allow the user to select an applicable status for the biliary dilatation according to their evaluation of image 1802.

In some instances, a user selects one of the selectable elements by providing manual user input (e.g., by providing touchscreen input, manipulating a mouse to move cursor 204 to select one of the status indicators 1804, etc.). In some instances, a user provides vocal input to select one of the status indicators, such as by selecting a microphone icon 1806 (or otherwise activating a dictation tool, as described herein) to provide a voice annotation that determines or can be used to determine an applicable status for the other finding (e.g., the biliary dilatation). The selected status for the other finding (e.g., the biliary dilatation), whether provided via voice annotation or via manual user input, may be used to modify metadata of the image 1802 to bind the status to the image 1802.

Figure 19:
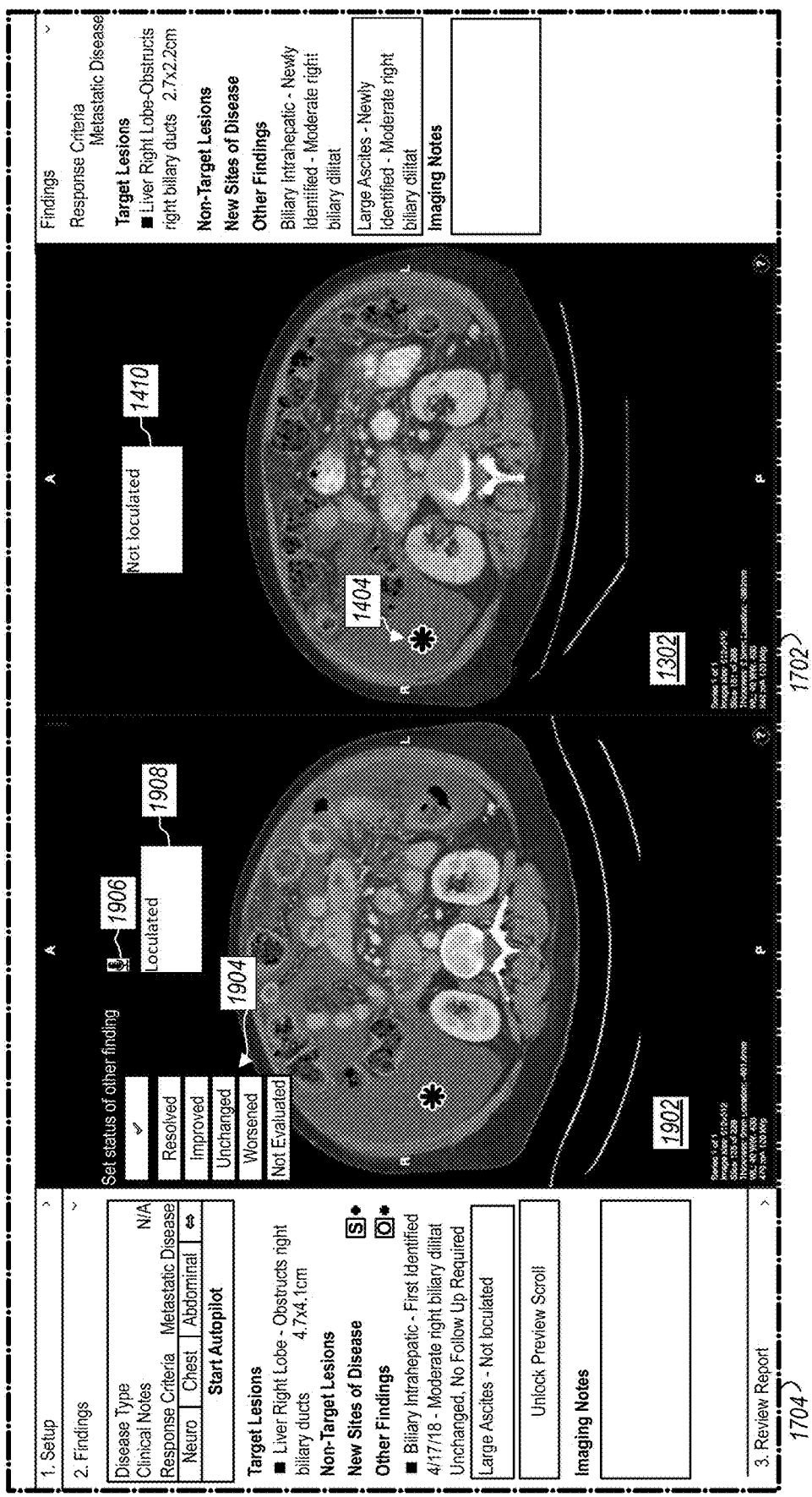
FIG. 19 illustrates an example of analyzing the other finding of FIGS. 13-15 in a corresponding subsequent-timepoint cross-sectional medical image.

In some instances, a user may determine that a previous dictation/description obtained in association with a first timepoint is no longer applicable or relevant to the structure as represented at a second timepoint. For example, a user may determine that a previous dictation/description needs to be altered or replaced to more accurately describe presence and/or status of the lesion/structure at the second timepoint. Accordingly, FIG. 19 illustrates longitudinal analysis of the ascites discussed hereinabove with reference to FIGS. 13-15. FIG. 19 illustrates the first user interface 1702 depicting image 1302 and attributes/characteristics of the finding (ascites) previously labeled in image 1302 (e.g., the label 1404, the voice annotation 1410, etc.). FIG. 19 also illustrates the second user interface 1704 illustrating image 1902 of the second set of images (e.g., image slice 125 of the 229 image slices), which depicts the same ascites at the second (e.g., later) timepoint. Similar to FIG. 18, FIG. 19 illustrates various selectable status indicators 1904 allowing the user to indicate a status of the biliary dilatation as represented at the second timepoint (e.g., in image 1902). FIG. 19 also illustrates a microphone icon 1906 that a user may select to activate a dictation tool to allow the user to provide a voice annotation indicating various details of the ascites as represented in image 1902. For example, the user may indicate that the ascites is "Loculated" at the second timepoint in contrast with voice annotation 1410 which indicates that the ascites was "Not loculated" at the first timepoint. Such an example dictation may be displayed to the user (e.g., as represented in FIG. 19 by the voice annotation 1908) contemporaneous with presentation of one or more of the images 1302 and 1902 and may be used to modify metadata of the image 1902 to bind the voice annotation 1908 to the image 1902. In view of the foregoing, a voice annotation may indicate status and/or presence of a structure in a subsequent-timepoint image to facilitate rapid, accurate longitudinal analysis. Similar to FIG. 16 shown above, a report may be generated that collects voice annotations (and/or other structure attributes/characteristics) from metadata and presents them to the user.

Example Method(s)

The following discussion now refers to a number of methods and method acts that may be performed by the disclosed systems. Although the method acts are discussed in a certain order and illustrated in a flow chart as occurring in a particular order, no particular ordering is required unless specifically stated, or required because an act is dependent on another act being completed prior to the act being performed. One will appreciate that certain embodiments of the present disclosure may omit one or more of the acts described herein.

Figure 20:
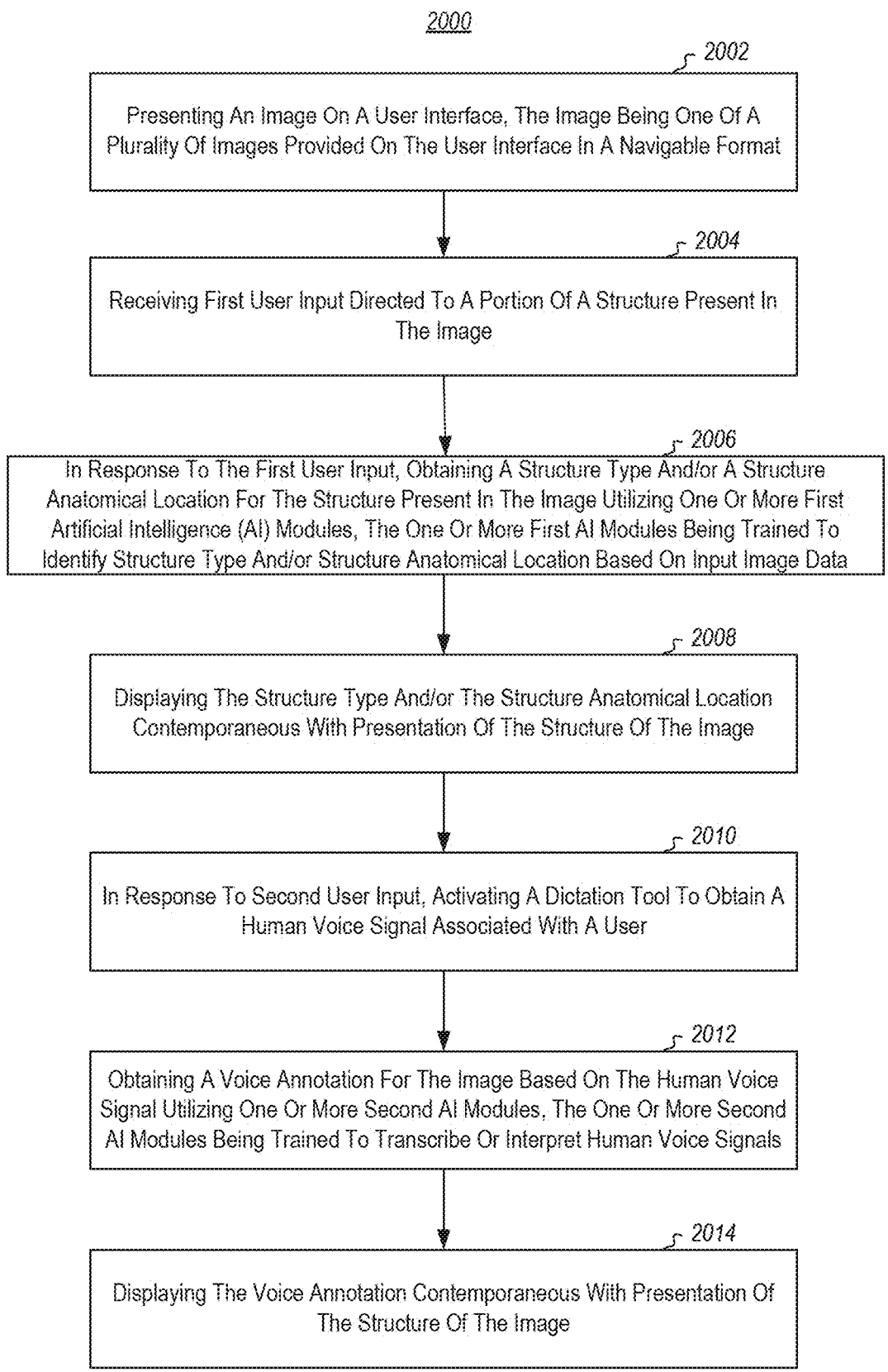
FIGS. 20-22 illustrate example flow diagrams depicting acts associated with the disclosed embodiments.
Figure 21:
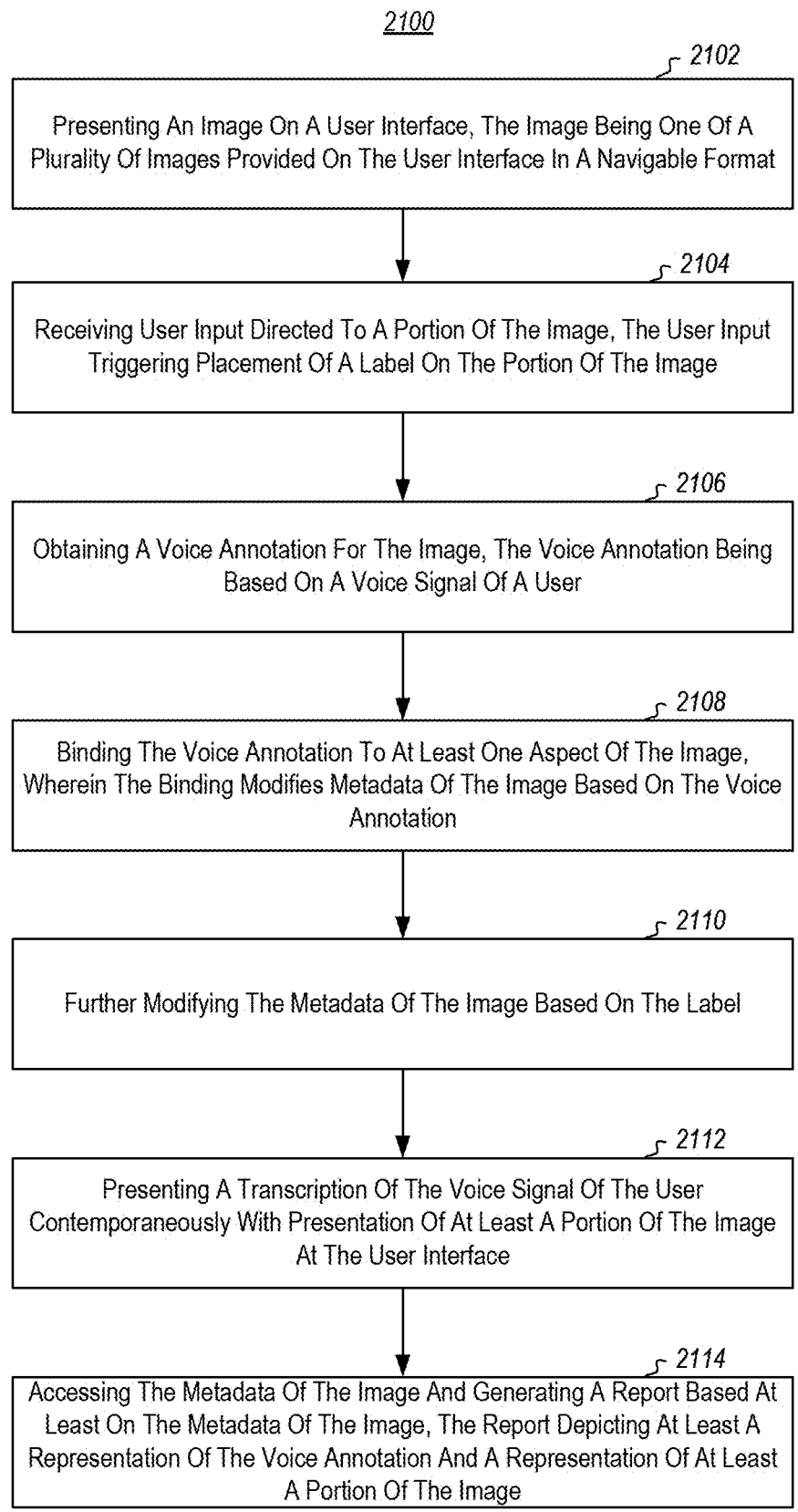
Figure 22:
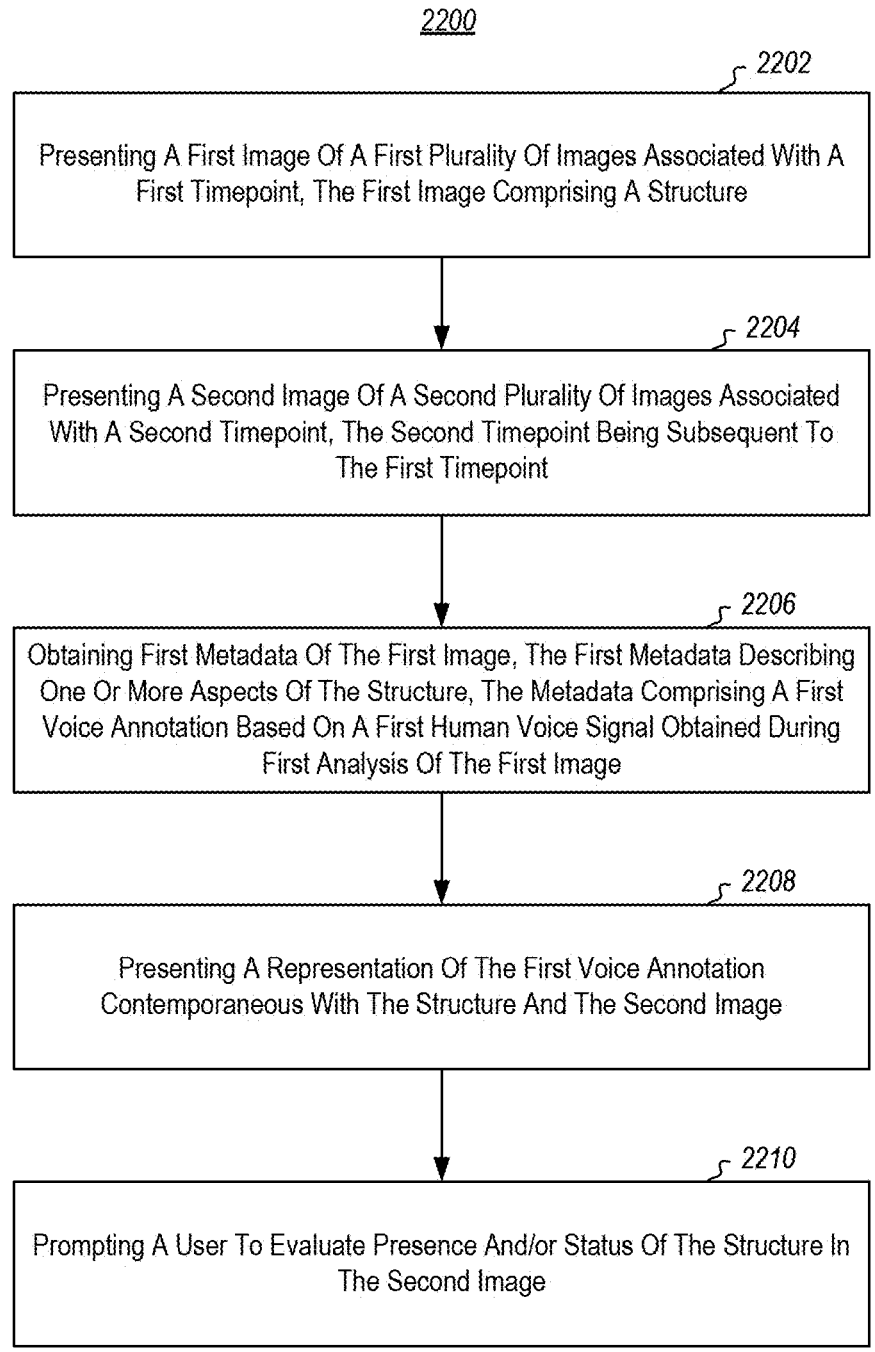

FIGS. 20, 21, and 22 illustrate example flow diagrams 2000, 2100, and 2200, respectively, depicting acts associated with facilitating image finding analysis. The various acts discussed herein may be performed utilizing one or more components of one or more systems discussed herein (e.g., computing system 100).

Act 2002 of flow diagram 2000 of FIG. 20 includes presenting an image on a user interface, the image being one of a plurality of images provided on the user interface in a navigable format. In some implementations, the image comprises a medical image such as a cross-sectional image (e.g., a CT image), which may comprise an image slice from a set of cross-sectional images.

Act 2004 of flow diagram 2000 includes receiving first user input directed to a portion of a structure present in the image. In some implementations, the first user input may comprise user selection input (e.g., clicking a mouse button, providing touch screen input) directed to a part of the image during presentation of the image on a user interface.

Act 2006 of flow diagram 2000 includes in response to the first user input, obtaining a structure type and/or a structure anatomical location for the structure present in the image utilizing one or more first artificial intelligence (AI) modules, the one or more first AI modules being trained to identify structure type and/or structure anatomical location based on input image data. The structure type and/or structure anatomical location for the structure may be automatically identified based on the first user input (e.g., based on image data associated with the portion of the structure present in the image and/or the image itself). In some instances, segmentation of the structure and/or one or more axis measurements of the structure is/are additionally or alternatively obtained via the one or more first AI modules.

Act 2008 of flow diagram 2000 includes displaying the structure type and/or the structure anatomical location contemporaneous with presentation of the structure of the image.

Act 2010 of flow diagram 2000 includes, in response to second user input, activating a dictation tool to obtain a human voice signal associated with a user. In some implementations, the second user input comprises selection of a selectable user interface element for activating the dictation tool. In some implementations, the dictation tool is automatically activated responsive to the first user input and/or responsive to acquisition/generation of the structure type and/or the structure anatomical location.

Act 2012 of flow diagram 2000 includes obtaining a voice annotation for the image based on the human voice signal utilizing one or more second AI modules, the one or more second AI modules being trained to transcribe or interpret human voice signals. Acquisition of the voice annotation for the image may be facilitated using the dictation tool, which, as noted above, may be activated responsive to the second user input (or the first user input and/or acquisition/generating of the structure type and/or the structure anatomical location; for instance, completion of processing by the one or more first AI module(s) to generate structure type and/or structure anatomical location information may cause activation of the dictation tool, or user input accepting or modifying the structure type and/or structure anatomical location information may cause activation of the dictation tool).

Act 2014 of flow diagram 2000 includes displaying the voice annotation contemporaneous with presentation of the structure of the image.

Act 2102 of flow diagram 2100 of FIG. 21 includes presenting an image on a user interface, the image being one of a plurality of images provided on the user interface in a navigable format. In some implementations, the plurality of images comprises a plurality of cross-sectional medical images.

Act 2104 of flow diagram 2100 includes receiving user input directed to a portion of the image, the user input triggering placement of a label on the portion of the image. In some implementations, the portion of the image corresponds to a structure present in the image. In some instances, the user input directed to the portion of the image comprises a user selection of the portion of the image. The placement of the label may trigger automatic identification of one or more structure attributes using one or more artificial intelligence (AI) modules, and the label may represent the one or more structure attributes. In some implementations, the structure comprises one or more of a mass, lymph node, metastasis, or other bodily structure captured in a plurality of cross-sectional medical images. In some implementations, the one or more structure attributes comprise anatomic location, lesion type, lesion measurements, or lesion segmentation.

Act 2106 of flow diagram 2100 includes obtaining a voice annotation for the image, the voice annotation being based on a voice signal of a user. In some instances, the voice signal is detected contemporaneous with presentation of at least a portion of the image at the user interface. In some implementations, obtaining the voice annotation comprises: activating a dictation tool in response to user input to capture the voice signal of the user, and generating the voice annotation based on the voice signal of the user. The voice annotation may comprise a transcription of the voice signal of the user. The voice annotation may comprise a selection of one or more predefined structure attributes. Obtaining the voice annotation for the image may comprises activating a dictation tool in response to the user input directed to the portion of the image (e.g., the portion of the image selected in accordance with act 2104).

Act 2108 of flow diagram 2100 includes binding the voice annotation to at least one aspect of the image, wherein the binding modifies metadata of the image based on the voice annotation.

Act 2110 of flow diagram 2100 includes further modifying the metadata of the image based on the label (e.g., the label of act 2104, or information associated with the label).

Act 2112 of flow diagram 2100 includes presenting a transcription of the voice signal of the user contemporaneously with presentation of at least a portion of the image at the user interface.

Act 2114 of flow diagram 2100 includes accessing the metadata of the image and generating a report based at least on the metadata of the image, the report depicting at least a representation of the voice annotation and a representation of at least a portion of the image.

In some implementations, the image and the voice annotation bound to one or more aspects of the image are configured as training data usable to train one or more AI modules for determining attributes of other images. For example, voice annotations that characterize or label certain structures within the image may be used to train one or more AI modules to associate such characteristics and/or labels with features of the image, such that future images that include such image features may be more readily associated with common characteristics and/or labels.

Act 2202 of flow diagram 2200 of FIG. 22 includes presenting a first image of a first plurality of images associated with a first timepoint, the first image comprising a structure. The first image may comprise a cross-sectional medical image, and the structure may comprise a bodily structure of a patient.

Act 2204 of flow diagram 2200 includes presenting a second image of a second plurality of images associated with a second timepoint, the second timepoint being subsequent to the first timepoint. The second image may comprise a cross-sectional medical image of a same patient represented in the first image.

Act 2206 of flow diagram 2200 includes obtaining first metadata of the first image, the first metadata describing one or more aspects of the structure, the metadata comprising a first voice annotation based on a first human voice signal obtained during first analysis of the first image. The first voice annotation may be obtained in accordance with one or more acts of flow diagram 2000 and/or 2100 discussed above.

Act 2208 of flow diagram 2200 includes presenting a representation of the first voice annotation contemporaneous with the structure and the second image. In some implementations, presenting the representation of the first voice annotation comprises emitting an audio signal representing the first voice annotation. In some instances, the representation of the first voice annotation is depicted visually.

Act 2210 of flow diagram 2200 includes prompting a user to evaluate presence and/or status of the structure in the second image. For example, the user may be prompted to evaluate whether characteristics and/or aspects/labels of the structure as depicted in the second image are different from characteristics and/or aspects/labels of the structure as depicted in the first image. Act 2210 may include, for example, prompting the user to provide a second human voice signal (where the second voice signal indicates the presence and/or status of the structure in the second image), generating a second voice annotation based on the second human voice signal, and modifying second metadata of the second image based on the second voice annotation. In some instances, the second metadata of the second image is modified with the first voice annotation, such as where a user indicates that the structure exhibits a status in the second image that is similar to that of the first image (e.g., by the user providing voice input such as "no change" or by providing other input).

Example Embodiments

The principles, components, concepts, and techniques discussed herein may be implemented in a variety of manners. The following provides various example, non-limiting embodiments that may implement various principles, components, concepts, and/or techniques discussed herein.

A first embodiment includes a system for facilitating image finding analysis, the system comprising: one or more processors; and one or more hardware storage devices storing instructions that are executable by the one or more processors to configure the system to: present an image on a user interface, the image being one of a plurality of images provided on the user interface in a navigable format; obtain a voice annotation for the image, the voice annotation being based on a voice signal of a user; and bind the voice annotation to at least one aspect of the image, wherein the binding modifies metadata of the image based on the voice annotation.

A second embodiment includes the system of embodiment 1, wherein the plurality of images comprises a plurality of cross-sectional medical images.

A third embodiment includes the system of any one of embodiments 1-2, wherein the voice signal is detected contemporaneous with presentation of at least a portion of the image at the user interface.

A fourth embodiment includes the system of any one of embodiments 1-3, wherein obtaining the voice annotation comprises: activating a dictation tool in response to user input to capture the voice signal of the user; and generating the voice annotation based on the voice signal of the user.

A fifth embodiment includes the system of any one of embodiments 1-4, wherein the voice annotation comprises a transcription of the voice signal of the user.

A sixth embodiment includes the system of any one of embodiments 1-5, wherein the voice annotation comprises a selection of one or more predefined structure attributes.

A seventh embodiment includes the system of any one of embodiments 1-6, wherein the instructions are executable by the one or more processors to further configure the system to: present a transcription of the voice signal of the user contemporaneously with presentation of at least a portion of the image at the user interface.

An eighth embodiment includes the system of any one of embodiments 1-7, wherein the instructions are executable by the one or more processors to further configure the system to: receive user input directed to a portion of the image, the user input triggering placement of a label on the portion of the image.

A ninth embodiment includes the system of embodiment 8, wherein the portion of the image corresponds to a structure present in the image.

A tenth embodiment includes the system of any one of embodiments 8-9, wherein the user input directed to the portion of the image comprises a user selection of the portion of the image.

An eleventh embodiment includes the system of embodiment 10, wherein the placement of the label triggers automatic identification of one or more structure attributes using one or more artificial intelligence (AI) modules, and wherein the label represents the one or more structure attributes.

A twelfth embodiment includes the system of embodiment 11, wherein: the plurality of images comprises a plurality of cross-sectional medical images; the structure comprises one or more of a mass, lymph node, metastasis, or other bodily structure captured in the plurality of cross-sectional medical images; and the one or more structure attributes comprise anatomic location, lesion type, lesion measurements, or lesion segmentation.

A thirteenth embodiment includes the system of any one of embodiments 8-12, wherein obtaining the voice annotation for the image comprises activating a dictation tool in response to the user input directed to the portion of the image.

A fourteenth embodiment includes the system of any one of embodiments 8-13, wherein the instructions are executable by the one or more processors to further configure the system to: further modify the metadata of the image based on the label.

A fifteenth embodiment includes the system of any one of embodiments 1-14, wherein the instructions are executable by the one or more processors to further configure the system to: access the metadata of the image; and generate a report based at least on the metadata of the image, the report depicting at least a representation of the voice annotation and a representation of at least a portion of the image.

A sixteenth embodiment includes the system of any one of embodiments 1-15, wherein the image and the voice annotation bound to one or more aspects of the image are configured as training data usable to train one or more AI modules for determining attributes of other images.

A seventeenth embodiment includes a system for facilitating image finding analysis, comprising: one or more processors; and one or more hardware storage devices storing computer-executable instructions that are executable by the one or more processors to configure the system to: present an image on a user interface, the image being one of a plurality of images provided on the user interface in a navigable format; receive first user input directed to a portion of a structure present in the image; in response to the first user input, obtain a structure type and/or a structure anatomical location for the structure present in the image utilizing one or more first artificial intelligence (AI) modules, the one or more first AI modules being trained to identify structure type and/or structure anatomical location based on input image data; display the structure type and/or the structure anatomical location contemporaneous with presentation of the structure of the image; in response to second user input, activate a dictation tool to obtain a human voice signal associated with a user; obtain a voice annotation for the image based on the human voice signal utilizing one or more second AI modules, the one or more second AI modules being trained to transcribe human voice signals; and display the voice annotation contemporaneous with presentation of the structure of the image.

An eighteenth embodiment includes the system of embodiment 17, wherein the second user input comprises selection of a selectable user interface element for activating the dictation tool.

A nineteenth embodiment includes the system of any one of embodiments 17-18 wherein the instructions are executable by the one or more processors to further configure the system to: in response to the first user input, obtain a segmentation of the structure and/or one or more axis measurements of the structure.

A twentieth embodiment includes a system for facilitating image finding analysis, the system comprising: one or more processors; and one or more hardware storage devices storing computer-executable instructions that are executable by the one or more processors to configure the system to: present a first image of a first plurality of images associated with a first timepoint, the first image comprising a structure; present a second image of a second plurality of images associated with a second timepoint, the second timepoint being subsequent to the first timepoint; obtain first metadata of the first image, the first metadata describing one or more aspects of the structure, the metadata comprising a first voice annotation based on a first human voice signal obtained during first analysis of the first image; present a representation of the first voice annotation contemporaneous with the structure and the second image; and prompt a user to evaluate presence and/or status of the structure in the second image.

A twenty-first embodiment includes the system of embodiment 20, wherein presenting the representation of the first voice annotation comprises emitting an audio signal representing the first voice annotation.

A twenty-second embodiment includes the system of any one of embodiments 20-21, wherein the instructions are executable by the one or more processors to configure the system to: modify second metadata of the second image with the first voice annotation.

A twenty-third embodiment includes the system of any one of embodiments 20-22, wherein the instructions are executable by the one or more processors to configure the system to: prompt the user to provide a second human voice signal; generate a second voice annotation based on the second human voice signal; and modify second metadata of the second image based on the second voice annotation.

A twenty-fourth embodiment includes the system of embodiment 23, wherein the second voice signal indicates the presence and/or status of the structure in the second image.

Additional Details Concerning Computing Systems

The principles disclosed herein may be implemented in various formats. For example, the various techniques discussed herein may be performed as a method that includes various acts for achieving particular results or benefits. In some instances, the techniques discussed herein are represented in computer-executable instructions that may be stored on one or more hardware storage devices. The computer-executable instructions may be executable by one or more processors to carry out (or to configure a system to carry out) the disclosed techniques. In some embodiments, a system may be configured to send the computer-executable instructions to a remote device to configure the remote device for carrying out the disclosed techniques.

As noted above, a computing system 100 may include and/or be used to perform any of the operations described herein. Computing system 100 may take various different forms. For example, computing system 100 may be embodied as a tablet, a desktop, a laptop, a mobile device, a cloud device, a head-mounted display, or a standalone device. Computing system 100 may also be a distributed system that includes one or more connected computing components/devices that are in communication with computing system 100.

Regarding the hardware processor(s) 108, it will be appreciated that the functionality described herein can be performed, at least in part, by one or more hardware logic components (e.g., the processor(s) 108). That is, any of the disclosed method acts and/or operations may be performed by the processor(s) 108. Illustrative types of hardware logic components/processors that can be used include Field-Programmable Gate Arrays ("FPGA"), Program-Specific or Application-Specific Integrated Circuits ("ASIC"), Program-Specific Standard Products ("ASSP"), System-On-A-Chip Systems ("SOC"), Complex Programmable Logic Devices ("CPLD"), Central Processing Units ("CPU"), Graphical Processing Units ("GPU"), or any other type of programmable hardware.

Hardware storage device(s) 112 may be physical system memory, which may be volatile, non-volatile, or some combination of the two. The term "memory" may also be used herein to refer to non-volatile mass storage such as physical storage media. If computing system 100 is distributed, the processing, memory, and/or storage capability may be distributed as well.

The disclosed embodiments may comprise or utilize a special-purpose or general-purpose computer including computer hardware, such as, for example, one or more processors (such as hardware processor(s) 108) and system memory (such as hardware storage device(s) 112), as discussed in greater detail below. Embodiments also include physical and other computer-readable media for carrying or storing computer-executable instructions and/or data structures. Such computer-readable media can be any available media that can be accessed by a general-purpose or special-purpose computer system. Computer-readable media that store computer-executable instructions in the form of data are "physical computer storage media" or a "hardware storage device." Computer-readable media that carry computer-executable instructions are "transmission media." Thus, by way of example and not limitation, the current embodiments can comprise at least two distinctly different kinds of computer-readable media: computer storage media and transmission media.

Computer storage media (aka "hardware storage device") are computer-readable hardware storage devices, such as RAM, ROM, EEPROM, CD-ROM, solid state drives ("SSD") that are based on RAM, Flash memory, phase-change memory ("PCM"), or other types of memory, or other optical disk storage, magnetic disk storage or other magnetic storage devices, or any other medium that can be used to store desired program code means in the form of computer-executable instructions, data, or data structures and that can be accessed by a general-purpose or special-purpose computer.

Computing system 100 may also be connected (via a wired or wireless connection) to external sensors (e.g., one or more remote radiologic devices 104) or devices via a network 128. For example, computing system 100 can communicate with any number devices or cloud services to obtain or process data. In some cases, network 128 may itself be a cloud network. Furthermore, computing system 100 may also be connected through one or more wired or wireless networks 128 to remote/separate computer systems(s) that are configured to perform any of the processing described with regard to computing system 100.

A "network," like network 128, is defined as one or more data links and/or data switches that enable the transport of electronic data between computer systems, modules, and/or other electronic devices. When information is transferred, or provided, over a network (either hardwired, wireless, or a combination of hardwired and wireless) to a computer, the computer properly views the connection as a transmission medium. Computing system 100 will include one or more communication channels that are used to communicate with the network 128. Transmissions media include a network that can be used to carry data or desired program code means in the form of computer-executable instructions or in the form of data structures. Further, these computer-executable instructions can be accessed by a general-purpose or special-purpose computer. Combinations of the above should also be included within the scope of computer-readable media.

Upon reaching various computer system components, program code means in the form of computer-executable instructions or data structures can be transferred automatically from transmission media to computer storage media (or vice versa). For example, computer-executable instructions or data structures received over a network or data link can be buffered in RAM within a network interface module (e.g., a network interface card or "NIC") and then eventually transferred to computer system RAM and/or to less volatile computer storage media at a computer system. Thus, it should be understood that computer storage media can be included in computer system components that also (or even primarily) utilize transmission media.

Computer-executable (or computer-interpretable) instructions comprise, for example, instructions that cause a general-purpose computer, special-purpose computer, or special-purpose processing device to perform a certain function or group of functions. The computer-executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Those skilled in the art will appreciate that the embodiments may be practiced in network computing environments with many types of computer system configurations, including personal computers, desktop computers, laptop computers, message processors, hand-held devices, multi-processor systems, microprocessor-based or programmable consumer electronics, network PCs, minicomputers, mainframe computers, mobile telephones, PDAs, pagers, routers, switches, and the like. The embodiments may also be practiced in distributed system environments where local and remote computer systems that are linked (either by hardwired data links, wireless data links, or by a combination of hardwired and wireless data links) through a network each perform tasks (e.g. cloud computing, cloud services and the like). In a distributed system environment, program modules may be located in both local and remote memory storage devices.

The concepts and features described herein may be embodied in other specific forms without departing from their spirit or descriptive characteristics. The described embodiments are to be considered in all respects only as illustrative and not restrictive. The scope of the disclosure is, therefore, indicated by the appended claims rather than by the foregoing description. All changes which come within the meaning and range of equivalency of the claims are to be embraced within their scope.

We claim:

1. A system for facilitating image finding analysis, comprising:
   one or more processors; and
   one or more hardware storage devices storing computer-executable instructions that are executable by the one or more processors to configure the system to:
   present an image on a user interface, the image being one of a plurality of images provided on the user interface in a navigable format;
   receive first user input directed to a portion of a structure present in the image;
   in response to the first user input, automatically obtain a structure type and a structure anatomical location for the structure present in the image utilizing one or more first artificial intelligence (AI) modules, the one or more first AI modules being trained to identify structure type and structure anatomical location based on input image data;
   in response to second user input, activate a dictation tool to obtain a human voice signal associated with a user;
   obtain a voice annotation for the image based on the human voice signal utilizing one or more second AI modules, the one or more second AI modules being trained to transcribe human voice signals; and
   display the voice annotation, the structure type, and the structure anatomical location contemporaneous with presentation of the structure of the image.

2. The system of claim 1, wherein the second user input comprises selection of a selectable user interface element for activating the dictation tool.

3. The system of claim 1, wherein the instructions are executable by the one or more processors to further configure the system to:
   in response to the first user input, obtain a segmentation of the structure and/or one or more axis measurements of the structure.

4. The system of claim 1, wherein the voice annotation, the structure type, and the structure anatomical location are displayed contemporaneous with presentation of the structure of the image of the plurality of images provided on the user interface in the navigable format, wherein the plurality of images comprises a set of cross-sectional medical images of a patient.

5. The system of claim 1, wherein the plurality of images comprises a plurality of cross-sectional medical images.

6. The system of claim 5, wherein the structure comprises one or more of a mass, a lymph node, a metastasis, or other bodily structure captured in the plurality of cross-sectional medical images.

7. The system of claim 1, wherein the voice annotation is obtained contemporaneous with presentation of the structure of image on the user interface.

8. The system of claim 1, wherein the first user input directed to the portion of the structure present in the image comprises a user selection of the portion of the structure present in the image.

9. The system of claim 8, wherein the user selection of the portion of the structure present in the image triggers placement of a label on the image indicating at least the structure type and the structure anatomical location.

10. The system of claim 1, wherein the instructions are executable by the one or more processors to further configure the system to:
    bind the voice annotation to at least one aspect of the image, wherein the binding modifies metadata of the image based on the voice annotation.

11. The system of claim 10, wherein the voice annotation comprises a text transcription of the human voice signal associated with the user.

12. The system of claim 11, wherein the image and the voice annotation bound to the at least one aspect of the image are configured as training data usable to train one or more AI modules for determining attributes of other images.

13. A system for facilitating image finding analysis, the system comprising:
    one or more processors; and
    one or more hardware storage devices storing computer-executable instructions that are executable by the one or more processors to configure the system to:
    present a first image of a first plurality of images associated with a first timepoint, the first image comprising a structure;
    present a second image of a second plurality of images associated with a second timepoint, the second timepoint being subsequent to the first timepoint, the second image of the second plurality of images being presented in navigable form, the second plurality of images comprising a set of cross-sectional medical images of a patient;

obtain first metadata of the first image, the first metadata describing one or more aspects of the structure, the first metadata comprising a first voice annotation based on a first human voice signal obtained during first analysis of the first image;

present a representation of the first voice annotation contemporaneous with the structure and the second image, the second image of the second plurality of images being presented in navigable form; and prompt a user to evaluate presence and/or status of the structure in the second image.

14. The system of claim 13, wherein the first metadata further comprises structure type and structure anatomical location for the structure.

15. The system of claim 14, wherein the instructions are executable by the one or more processors to further configure the system to:

present a representation of the structure type and the structure anatomical location for the structure contemporaneous with the structure and the second image.

16. The system of claim 13, wherein the first metadata further comprises a segmentation of the structure and/or one or more axis measurements of the structure.

17. The system of claim 16, wherein the instructions are executable by the one or more processors to further configure the system to:

present a representation of the segmentation and the one or more axis measurements contemporaneous with the structure and the second image.

18. The system of claim 13, wherein the structure comprises one or more of a mass, a lymph node, a metastasis, or other bodily structure.

19. The system of claim 13, wherein the instructions are executable by the one or more processors to further configure the system to:

obtain a second voice annotation for the second image based on a second human voice signal, wherein the second voice annotation indicates the presence and/or status of the structure in the second image.

20. The system of claim 19, wherein the instructions are executable by the one or more processors to further configure the system to:

bind the second voice annotation to at least one aspect of the second image, wherein the binding modifies second metadata of the second image based on the second voice annotation.

* * * * *